United States Patent
Shimizu et al.

(10) Patent No.: US 6,716,621 B1
(45) Date of Patent: Apr. 6, 2004

(54) ISOLATED DNA OR GENE RESPONSIBLE FOR PARKINSON'S DISEASE

(75) Inventors: Nobuyoshi Shimizu, Sakura (JP); Yoshikuni Mizuno, Tokyo-to (JP)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 09/601,844

(22) PCT Filed: Feb. 9, 1999

(86) PCT No.: PCT/JP99/00545

§ 371 (c)(1),
(2), (4) Date: Aug. 9, 2000

(87) PCT Pub. No.: WO99/40191

PCT Pub. Date: Aug. 12, 1999

(30) Foreign Application Priority Data

Feb. 9, 1998 (JP) .............................................. 10-27531

(51) Int. Cl.[7] .......................... C12N 15/74; C07H 21/04
(52) U.S. Cl. ................... 435/320.1; 536/23.1; 536/23.2
(58) Field of Search .............................. 536/23.1, 23.2; 435/69.1, 320.1

(56) References Cited

PUBLICATIONS

Kitada T., et al., "Mutations in the *parkin* gene cause autosomal recessive juvenile parkinsonism," *Nature 392* :605–608, Nature Publishing Group, (Apr. 1998).

Matsumine, H., et al., "Localization of a Gene of an Autosomal Recessive Form of Juvenile Parkinsonism to Chromosome 6q25.2–27," *Am. J. Hum. Genet. 60*(3):588–596, The University of Chicago Press, (Mar. 1997).

Saito, M., et al., "Refinement of the gene locus for autosomal recessive juvenile parkinsonism (AR–JP) on chromosome 6q25.2–27 and identification of markers exhibiting linkage disequilibrium," *Am. J. Hum. Genet. 61*(4), Abstract No. 1708, The University of Chicago Press, (Oct. 1997).

Shimoda–Matsubayashi, S., et al., "Mn SOD activity and protein in a patient with chromosome 6–linked autosomal recessive parkinsonism in comparison with Parkinson's disease and control," *Neurology 49* (5):1257–1262, American Academy of Neurology, (Nov. 1997).

*Primary Examiner*—Gary Kunz
*Assistant Examiner*—Sharon Turner
(74) *Attorney, Agent, or Firm*—Sterne, Kessler, Goldstein & Fox P.L.L.C.

(57) ABSTRACT

This invention provides an isolated DNA or gene that is responsible for Parkinson's disease and is useful in diagnosing and treating the disease etc.

The isolated DNA or gene according to this invention comprises a full-length base sequence according to the sequence ID. No. 1 or 2, or a partial sequence thereof, or a base sequence hybridizable thereto or hybridizable with a complemental strand thereof, and being associated with Parkinson's disease.

12 Claims, 25 Drawing Sheets

(9 of 25 Drawing Sheet(s) Filed in Color)

FIG. 5

```
Parkin              Met Ile Val Phe Val Arg Phe Asn Ser Ser His Gly Phe Pro Val Asp Ser Asp
UBIQUITIN HUMAN     Met Gln Ile Phe Val Lys Thr Leu Thr Gyl Lys Thr Ile Thr Leu Glu Val Glu Pro Ser
UBIQUITIN YEAST     Met Gln Ile Phe Val Lys Thr Leu Thr Gyl Lys Thr Ile Thr Leu Glu Val Glu Ser Ser
UBIQUITIN SOYBEAN   Met Gln Ile Phe Val Lys Thr Leu Thr Gyl Lys Thr Ile Thr Leu Glu Val Glu Ser Ser
                                      5                        10                      15         20

Parkin              Thr Ser Ile Phe Gln Leu Lys Glu Val Val Ala Lys Arg Gln Gly Val Pro Ala Asp Gln
UBIQUITIN HUMAN     Asp Thr Ile Glu Asn Val Lys Ala Lys Ile Gln Asp Lys Glu Gly Ile Pro Pro Asp Gln
UBIQUITIN YEAST     Asp Thr Ile Asp Asn Val Lys Ser Lys Ile Gln Asp Lys Glu Gly Ile Pro Pro Asp Gln
UBIQUITIN SOYBEAN   Asp Thr Ile Asp Asn Val Lys Ala Lys Ile Gln Asp Lys Glu Gly Ile Pro Pro Asp Gln
                                      25                       30                      35         40

Parkin              Leu Arg Val Ile Phe Ala Gly Lys Glu Leu Arg Asn Asp Trp Thr Val Gln Asn Cys Asp
UBIQUITIN HUMAN     Gln Arg Leu Ile Phe Ala Gly Lys Gln Leu Glu Asp Gly Arg Thr Leu Ser Asp Tyr Asn
UBIQUITIN YEAST     Gln Arg Leu Ile Phe Ala Gly Lys Gln Leu Glu Asp Gly Arg Thr Leu Ser Asp Tyr Asn
UBIQUITIN SOYBEAN   Gln Arg Leu Ile Phe Ala Gly Lys Gln Leu Glu Asp Gly Arg Thr Leu Ala Asp Tyr Asn
                                      45                       50                      55         60

Parkin              Leu Asp Gln Gln Ser Ile Val His Ile Val Gln Arg Pro Trp Arg Lys
UBIQUITIN HUMAN     Ile Gln Lys Glu Ser Thr Leu His Leu Val Leu Arg Leu Arg Gly Gly
UBIQUITIN YEAST     Ile Gln Lys Glu Ser Thr Leu His Leu Val Leu Arg Leu Arg Gly Gly
UBIQUITIN SOYBEAN   Ile Gln Lys Glu Ser Thr Leu His Leu Val Leu Arg Leu Arg Gly Gly
                                      65                       70                      75
```

(1) Exon 3

(2) Exon 4 inner (3) Exon 4 outer (4) Exon 5

```
          intron 4→||←Exon 5
                    640             650             660
Normal tcccaaag GGT CCA TCT TGC TGG GAT GAT GTT TTA ATT
                Gly Pro Ser Cys Trp Asp Asp Val Leu Ile Mutant tcccaaag GTC CAT CTT GCT GGG ATG ATG TTT TAA TT
                Val His Leu Ala Gly Met Met Phe ***
```

ISOLATED DNA OR GENE RESPONSIBLE FOR PARKINSON'S DISEASE

This application is a 35 U.S.C. § 371 national stage application of the international application, PCT/JP99/00545, filed Feb. 9, 1999, which claims priority benefit to Japanese application no. 10/27531, filed Feb. 9, 1998, the full disclosures of which are herein incorporated by reference.

TECHNICAL FIELD

The present invention relates to a gene responsible for onset of Parkinson's disease. Since it was found that Parkinson's disease patients have a deletion in part of the gene, the gene of this invention is significantly useful as a gene for diagnosing Parkinson's disease, and a protein and a pharmaceutically active agent etc., obtainable from the inventive gene has usability in preventing and treating Parkinson's disease.

BACKGROUND ART

Generally, it is often considered that one or more gene is responsible for various chronic progressive diseases. Isolating the gene or genes responsible for these diseases not only enables one to facilitate prenatal or postnatal diagnosis but also enables to perform gene therapy for the disease based on the remarkable progress and development of gene therapy as seen today.

Parkinson's disease is a chronic disease. α-synuclein reported in 1997 has so far been the only gene that has been found to be responsible for Parkinson's disease. It is reported that some people having Italian ancestry suffer from autosomal dominant Parkinson's disease due to mutation of this gene. There is, however, limitation in diagnosing Parkinson's disease even with use of this gene. Therefore, what has been adopted at present as a diagnosis for Parkinson's disease is merely a clinical approach based on neurodegenerative symptoms such as resting tremor, rigidity, akinesia, and disturbance of the righting ref lux, and a levodopa-responsive or dopaminergic compound (agonist) has been administered as a symptomatic treatment. So far no drastic therapy has been performed for treating Parkinson's disease.

DISCLOSURE OF THE INVENTION

The present invention has been made in view of the above. An object of this invention is to provide an isolated DNA or gene or gene fragment that is responsible for Parkinson's disease and is useful in diagnosing and treating the disease etc.; a recombinant vector; a protein or polypeptide; a monoclonal antibody or polyclonal antibody; a primer or probe or immobilized nucleic acid or DNA chip; and an oligonucleotide, or the like.

The isolated DNA or gene according to this invention that has overcome the above problems residing in the prior art is:

① An isolated DNA or gene: comprising a full-length base sequence according to the SEQ ID. Nos. 1 or 3 (SEQ ID No. 3 does not include a base portion 636 to 719 (corresponding to exon 5 which is described later) of SEQ ID. No. 1, namely, a variant thereof according to alternative splicing), or a partial sequence thereof, or a base sequence hybridizable thereto or hybridizable with a complementary strand thereof, and being associated with Parkinson's disease.

Further, the inventive DNA or gene may include a DNA or gene or gene fragment having the following features ② to ⑧, in addition to ①.

② An isolated DNA or gene: comprising the base sequence of ①, or the full-length base sequence thereof, or the base sequence partially thereof, and the isolated DNA or gene whose gene defect is responsible for Parkinson's disease, or comprising a base sequence hybridizable thereto or hybridizable with a complementary strand thereof.

An isolated DNA or gene comprising the base sequence of ① or ②, the isolated DNA or gene being variant thereof by alternative splicing, and being associated with Parkinson's disease, or the isolated DNA or gene comprising a base sequence hybridizable thereto or hybridizable with a complementary strand thereof.

④ A gene comprising the base sequence of any one of ① to ③ whose gene product encodes a protein having a substantially equivalent function to a protein comprising amino acids 1 to 465 of SEQ ID. No. 2 or a protein comprising amino acids 1 to 437 of SEQ ID. No. 4.

⑤ An isolated DNA or gene comprising a gene where an exonic deletion, a nonsense base substitute, a missense base substitute, a base deletion, a base addition, a base insertion, a splicing abnormality and/or a frameshift with respect to the base sequence has occurred in any one of ① to ④; or comprising a base sequence hybridizable thereto or hybridizable with a, complementary strand thereof, and the isolated DNA or gene being associated with Parkinson's disease.

⑥ An isolated DNA or a gene, or a gene fragment comprising a partial base sequence of the DNA or the gene of any one of claims ① to ⑤, or an isolated DNA or a gene or a gene fragment comprising a base sequence hybridizable thereto or hybridizable with a complementary strand thereof.

⑦ A gene encoding a protein (a) or (b) comprising:
(a) the protein comprising amino acids 1 to 465 of SEQ ID. No. 1;
(b) the protein in which one or more amino acid(s) of the amino acid sequence is or are deleted, substituted, or added, and the protein being associated with Parkinson's disease.

⑧ A gene encoding a protein (c) or (d):
(c) the protein comprising amino acids 1 to 437 of SEQ ID. No. 4;
(d) the protein in which one or more amino acid(s) of the amino acid sequence is or are deleted, substituted, or added, and the protein being associated with Parkinson's disease.

The full-length base sequence SEQ ID. No. 1 is such that eleven introns are intervened among twelve exons on the genome; and encodes a protein having 1 to 465 amino acid sequence in a part (102 to 1496) of the base sequence. The base sequence of the intron in a boundary region between the exon and the intron has the following arrangement:

the intron intervening between exon 1 and exon 2 has a base sequence shown in SEQ ID. No. 9 adjacent to the 3' end of the exon 1, and has a base sequence shown in SEQ ID. No. 10 adjacent to the 5' end of the exon 2;

the intron intervening between exon 2 and exon 3 has a base sequence shown in SEQ ID. No. 11 adjacent to the 3' end of the exon 2, and has a base sequence shown in SEQ ID. No. 12 adjacent to the 5' end of the exon 3;

the intron intervening between exon 3 and exon 4 has a base sequence shown in SEQ ID. No. 13 adjacent to the 3' end of the exon 3, and has a base sequence shown in SEQ ID. No. 14 adjacent to the 5' end of the exon 4;

the intron intervening between exon 4 and exon 5 has a base sequence shown in SEQ ID. No. 15 adjacent to the 3' end of the exon 4, and has a base sequence shown in SEQ ID. No. 16 adjacent to the 5' end of the exon 5;

the intron intervening between exon 5 and exon 6 has a base sequence shown in SEQ ID. No. 17 adjacent to the 3' end of the exon 5, and has a base sequence shown in SEQ ID. No. 18 adjacent to the 5' end of the exon 6;

the intron intervening between exon 6 and exon 7 has a base sequence shown in SEQ ID. No. 19 adjacent to the 3' end of the exon 6, and has a base sequence shown in SEQ ID. No. 20 adjacent to the 5' end of the exon 7;

the intron intervening between exon 7 and exon 8 has a base sequence shown in SEQ ID. No. 21 adjacent to the 3' end of the exon 7, and has a base sequence shown in SEQ ID. No. 22 adjacent to the 5' end of the exon 8;

the intron intervening between exon 8 and exon 9 has a base sequence shown in SEQ ID. No. 23 adjacent to the 3' end of the exon 8, and has a base sequence shown in SEQ ID. No. 24 adjacent to the 5' end of the exon 9;

the intron intervening between exon 9 and exon 10 has a base sequence shown in SEQ ID. No. 25 adjacent to the 3' end of the exon 9, and has a base sequence shown in SEQ ID. No. 26 adjacent to the 5' end of the exon 10;

the intron intervening between exon 10 and exon 11 has a base sequence shown in SEQ ID. No. 27 adjacent to the 3' end of the exon 10, and has a base sequence shown in SEQ ID. No. 28 adjacent to the 5' end of the exon 11; and the intron intervening between exon 11 and exon 12 has a base sequence shown in SEQ ID. No. 29 adjacent to the 3' end of the exon 11, and has a base sequence shown in SEQ ID. No. 30 adjacent to the 5' end of the exon 12.

In addition, a recombinant vector comprising the DNA fragment or the gene of any one of ① to ⑧ may be included in the scope of this invention.

The protein which has overcome the above problem is (i) a protein comprising amino acids 1 to 465 of SEQ ID. No. 1; or (ii) a protein comprising 1 to 437 amino acid sequence in the sequence ID. No. 2, the protein being associated with Parkinson's disease; or a protein having a substantially equivalent function thereto.

More specifically, the protein or polypeptide according to this invention may embrace the following aspects (ii) to (viii).

(ii) A protein expressed by the gene of any one of ① to ④, the protein being associated with Parkinson's disease, or having an identical function thereto or a substantially equivalent function thereto.

(iii) A protein comprising an amino acid sequence translated by the gene of ⑤, the protein being associated with Parkinson's disease, or having an identical function thereto or a substantially equivalent function thereto.

(iv) A protein comprising the amino acid sequence of (iii) in which an amino acid is substituted, deleted, or added at least at one position, and the protein being associated with Parkinson's disease.

(v) A protein comprising the amino acid sequence of any one of (ii) to (iv) comprising: a ubiquitin-like 1 to 72 amino acid sequence partially included in SEQ ID. No. 1; and a zinc-finger-protein-like 418 to 449 amino acid sequence partially included in SEQ ID. No. 1.

(vi) A protein (a) or (b):
(a) the protein comprising amino acids 1 to 465 of SEQ ID. No. 1;
(b) the protein in which one or more amino acid(s) of the amino acid sequence is or are deleted, substituted, or added, and the protein being associated with Parkinson's disease.

(vii) A protein (c) or (d):
(c) the protein comprising 1 to 437 ID. No. 2;
(d) the protein in which one or more amino acid(s) of the amino acid sequence is or are deleted, substituted, or added, and the protein being associated with Parkinson's disease.

(viii) A polypeptide or a protein consisting of a partial fragment of the amino acid sequence of any one of (i) (vii), or comprising the partial fragment thereof, or the full-length amino acid sequence thereof.

In addition, a monoclonal antibody or a polyclonal antibody against the protein of any one of (i) to (viii) may be included in the scope of this invention.

Further, a primer, or a probe, or an immobilized nucleic acid, or a DNA chip according to this invention may preferably be used for the following purposes (I) to (IV):

(I) for use in detecting a base sequence, a genetic mutation, a deletion, and/or an expression amount of the DNA or the gene of any one of ① to ⑧, or for use in concentration thereof;

(II) for use in detecting a base sequence, a genetic mutation, a deletion, and/or an expression amount of RNA which is subjected to transcription and subjected to processing from the DNA or the gene of any one of ① to ⑧, or for use in concentration thereof;

(III) for use in detecting a base sequence, a genetic mutation, and/or a deletion of the exon of SEQ ID. No. 1 or 3, or for use in haplotyping a locus thereof; or (IV) for use in detecting a base sequence, a genetic mutation, and/or a deletion of the aforemention intron, or for use in haplotyping a locus thereof.

Specifically, at least one of the fourteen sets of primers or probes shown in the following (1) to (14) can be used.

(1) A primer or a probe for use in detecting a base sequence of the intron adjacent to the exon 1 of the gene being associated with Parkinson's disease of ①, or a locus thereof, the primer or probe comprising the following base sequence:
a base sequence of SEQ ID. No. 31 in the 5'-3' direction of SEQ ID. No. 1 on the genome, and
a base sequence of SEQ ID. No. 32 in the 5'-3' direction on a complementary strand of SEQ ID. No. 1 on the genome.

(2) A primer or a probe for use in detecting a base sequence of an intron adjacent to the exon 2 of the gene being associated with Parkinson's disease of ①, or a locus thereof, the primer or the probe comprising the following base sequence:
a base sequence of SEQ ID. No. 33 in the 5'-3' direction of SEQ ID. No. 1 on the genome, and
a base sequence of SEQ ID. No. 34 in the 5'-3' direction on a complementary strand of SEQ ID. No. 1 on the genome.

(3) A primer or a probe f or use in detecting a base sequence of an intron adjacent to the exon 3 of the gene being associated with Parkinson's disease of ①, or a locus thereof, the primer or the probe comprising the following base sequence:
a base sequence of SEQ ID. No. 35 in the 5'-3' direction of SEQ ID. No. 1 on the genome, and
a base sequence of SEQ ID. No. 36 in the 5'-3' direction on a complementary strand of SEQ ID. No. 1 on the genome.

(4) A primer or a probe for use in detecting a base sequence of the intron adjacent to the exon 4 of the gene being associated with Parkinson's disease of (1), or a locus thereof, the primer or probe comprising the following base sequence:
a base sequence of SEQ ID. No. 37 in the 5'-3' direction of SEQ ID. No. 1 on the genome, and
a base sequence of SEQ ID. No. 38 in the 5'-3' direction on a complementary strand of SEQ ID. No. 1 on the genome.

(5) A primer or a probe for use in detecting a base sequence of an intron adjacent to the exon 4 of the gene being associated with Parkinson's disease of (1), or a locus thereof, the primer or the probe comprising the following base sequence:
a base sequence of SEQ ID. No. 39 in the 5'-3' direction of SEQ ID. No. 1 on the genome, and
a base sequence of SEQ ID.No. 40 in the 5'-3' direction on a complementary strand of SEQ ID. No. 1 on the genome.

(6) A primer or a probe for use in detecting a base sequence of an intron adjacent to the exon 5 of the gene being associated with Parkinson's disease of (1), or a locus thereof, the primer or the probe comprising the following base sequence:
a base sequence of SEQ ID. No. 41 in the 5'-3' direction of SEQ ID. No. 1 on the genome, and
a base sequence of SEQ ID. No. 42 in the 5'-3' direction on a complementary strand of SEQ ID. No. 1 on the genome.

(7) A primer or a probe for use in detecting a base sequence of the intron adjacent to the exon 6 of the gene being associated with Parkinson's disease of (1), or a locus thereof, the primer or probe comprising the following base sequence:
a base sequence of SEQ ID. No. 43 in the 5'-3' direction of SEQ ID. No. 1 on the genome, and
a base sequence of SEQ ID. No. 44 in the 5'-3' direction on a complementary strand of SEQ ID. No. 1 on the genome.

(8) A primer or a probe for use in detecting a base sequence of an intron adjacent to the exon 7 of the gene being associated with Parkinson's disease of (1), or a locus thereof, the primer or the probe comprising the following base sequence:
a base sequence of SEQ ID. No. 45 in the 5'-3' direction of SEQ ID. No. 1 on the genome, and
a base sequence of SEQ ID. No. 46 in the 5'-3' direction on a complementary strand of SEQ ID. No. 1 on the genome.

(9) A primer or a probe for use in detecting a base sequence of an intron adjacent to the exon 7 of the gene being associated with Parkinson's disease of (1), or a locus thereof, the primer or the probe comprising the following base sequence:
a base sequence of SEQ ID. No.47 in the 5'-3' direction of SEQ ID. No. 1 on the genome, and
a base sequence of SEQ ID. No. 48 in the 5'-3' direction on a complementary strand of SEQ ID. No. 1 on the genome.

(10) A primer or a probe for use in detecting a base sequence of the intron adjacent to the exon 8 of the gene being associated with Parkinson's disease of (1), or a locus thereof, the primer or probe comprising the following base sequence:
a base sequence of SEQ ID. No. 49 in the 5'-3' direction of SEQ ID. No. 1 on the genome, and
a base sequence of SEQ ID. No. 50 in the 5'-3' direction on a complementary strand of SEQ ID. No. 1 on the genome.

(11) A primer or a probe for use in detecting a base sequence of an intron adjacent to the exon 9 of the gene being associated with Parkinson's disease of (1), or a locus thereof, the primer or the probe comprising the following base sequence:
a base sequence of SEQ ID. No. 51 in the 5'-3' direction of SEQ ID. No. 1 on the genome, and
a base sequence of the SEQ ID. No. 52 in the 5'-3' direction on a complementary strand of SEQ ID. No. 1 on the genome.

(12) A primer or a probe for use in detecting a base sequence of an intron adjacent to the exon 10 of the gene being associated with Parkinson's disease of (1), or a locus thereof the primer or the probe comprising the following base sequence:
a base sequence of SEQ ID. No. 53 in the 5'-3' direction of SEQ ID. No. 1 on the genome, and
a base sequence of SEQ ID. No. 54 in the 5'-3' direction on a complementary strand of SEQ ID. No. 1 on the genome.

(13) A primer or a probe for use in detecting a base sequence of the intron adjacent to the exon 11 of the gene being associated with Parkinson's disease of (1), or a locus thereof, the primer or probe comprising the following base sequence:
a base sequence of SEQ ID. No. 55 in the 5'-3' direction of SEQ ID. No. 1 on the genome, and
a base sequence of SEQ ID. No. 56 in the 5'-3' direction on a complementary strand of SEQ ID. No. 1 on the genome.

(14) A primer or a probe for use in detecting a base sequence of an intron adjacent to the exon 12 of the gene being associated with Parkinson's disease of (1), or a locus thereof, the primer or the probe comprising the following base sequence:
a base sequence of SEQ ID. No. 57 in the 5'-3' direction of SEQ ID. No. 1 on the genome, and
a base sequence of SEQ ID. No. 58 in the 5'-3' direction on a complementary strand of SEQ ID. No. 1 on the genome.

Further, the present invention may include the following oligonucleotide, or an oligonucleotide analog, or a modified product thereof as shown in (a) to (c):

(a) the one which comprises a partial sequence of the base sequence of any one of (1) to (8), or which is hybridizable with the base sequence of any one of (1) to (8).

(b) the one for use in amplifying the full-length base sequence or the partial base sequence of any one of (1) to (8), or the oligonucleotide for use in amplifying partially the full-length base sequence or the partial base sequence of any one of (1) to (8), according to PCR method using a human RNA as a template, PCR method or RT-PCR method using a human cDNA as a template.

(c) the oligonucleotide for use in amplifying the base sequence comprising the exon in SEQ ID. No. 1 or No. 3 and the aforementioned intron which is adjacent to the exon according to PCR method, or the oligonucleotide for use in amplifying a part of the base sequence according to PCR method.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 5 is a diagram showing amino acid sequence homology between the N-terminus of this inventive gene and ubiquitin. The aligned sequences include Parkin (amino acids 1–76 of SEQ ID NO:2). Human Ubiquitin (SEQ ID NO:60), Yeast Ubiquitin (SEQ ID NO:61) and Soybean Ubiquitin (SEQ ID NO:62).

BEST MODE FOR CARRYING OUT THE INVENTION

Parkinson's disease or Parkinsonism is considered to be initiated by genetic predisposition and environmental factors. Elucidating individual factors is an urgent matter on fundamental understanding and treatment of Parkinson's disease and Parkinsonism in their onset stage. The inventors of this invention have studied to find out a gene responsible for onset of Parkinson's disease. As a result of their study, it was found that the region of chromosome 6q25.2-q27, more specifically, a 17-cM region between two chromosome markers DS437 and D6S264 has a strong linkage with juvenile Parkinsonism, which is one of the family of Parkinson's disease (Matsumine et al., Am. J. Hum. Genet. 60(1997)588–596). The inventors have succeeded in isolating the gene responsible for Parkinson's disease by conducting the below-mentioned Examples with respect to the juvenile Parkinson's disease patients and thus accomplished the present invention.

Hereinafter, the present invention is described in detail with reference to the process of experiments that have contributed to the finding of the inventive gene. It should be appreciated that the following examples are illustrative and not restrictive, and all changes that fall within metes and bounds of the claims, or equivalence of such metes and bounds are therefore intended to be embraced by the claims.

EXAMPLE 1

Chromosomal Deletion Region in Juvenile Parkinson's Disease Patient

Figure 1:
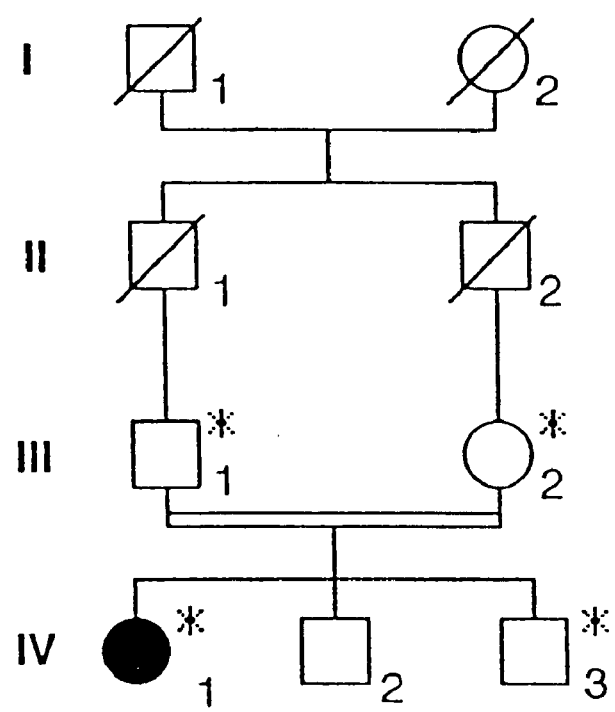
FIG. 1 is a diagram showing the pedigree of family members including Parkinson's disease patient in Example 1.

FIG. 1 shows the pedigree of family members including Parkinson's disease patient in Example 1. In FIG. 1, an open square represents an unaffected male, an open circle represents an unaffected female, and a filled circle represents the affected female. The circle or square with slash represents the deceased member. Although the parents and brothers of the patient are not affected, the patient had Parkinson-like symptom from her teens and diagnosed as Parkinson's disease. The symptom has been gradually progressing.

Haplotyping according to PCR method was performed using D6S305 which is one of the markers of chromosome 6 with respect to the genomic DNA of subjects marked with an asterisk in FIG. 1 (patient and two unaffected members). The result is shown in FIG. 2.

Figure 2:
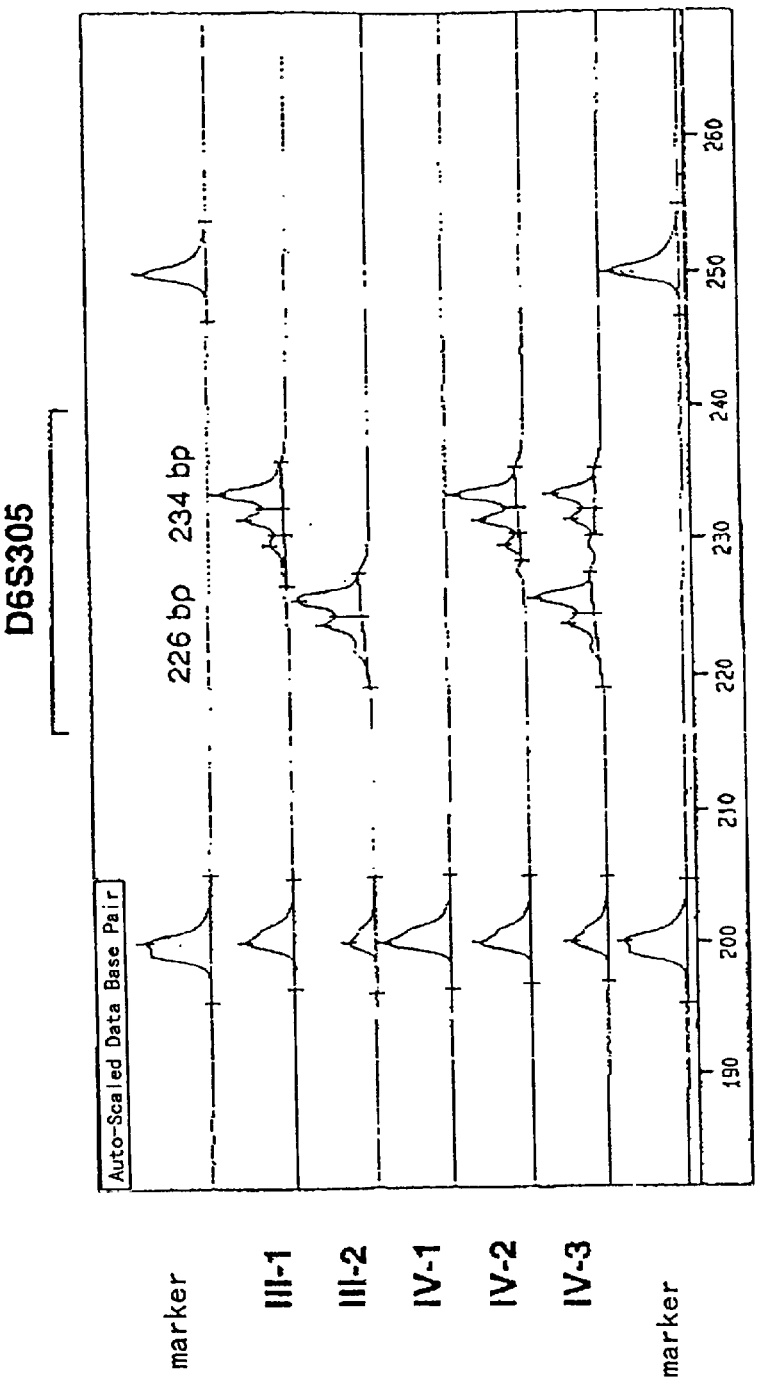
FIG. 2 is a diagram showing results of haplotyping according to PCR analysis with respect to the family members including Parkinson's disease patient in FIG. 1.

As shown in FIG. 2, D6S305 was amplified from DNA template of the parents and brother of the patient, however, D6S305 was not amplified from DNA template of the patient. It was verified accordingly that the patient has deletion of D6S305 which is one of the chromosomal markers.

EXAMPLE 2

Screening of Genomic Fragment Including D6S305 and Exon Trapping

Since Example 1 verified that the patient has deletion of the genomic DNA corresponding to marker D6S305, there is a possibility that a gene responsible for Parkinson's disease may exist on the genomic DNA. To verify the possibility, PCR screening was performed to isolate normal human genomic library consisting of 96,000 genomic fragment (the Keio human BAC library) using a set of amplimers having a sequence of part of marker D6S305. As a result of screening, two clones, genomic fragments KB761D4 and KB430C4 each of which has an insert size of about 110 kb were isolated.

Next, exon trapping was performed to isolate exon fragment of the gene existing on the genomic fragments using exon trapping system (provided by GIBCO/BRL) according to the manufacturer's instruction manual. As a result, the isolated exon was J-17 only despite the fact that the two genomic fragments each had a relatively large size of about 110 kb.

Figure 3:
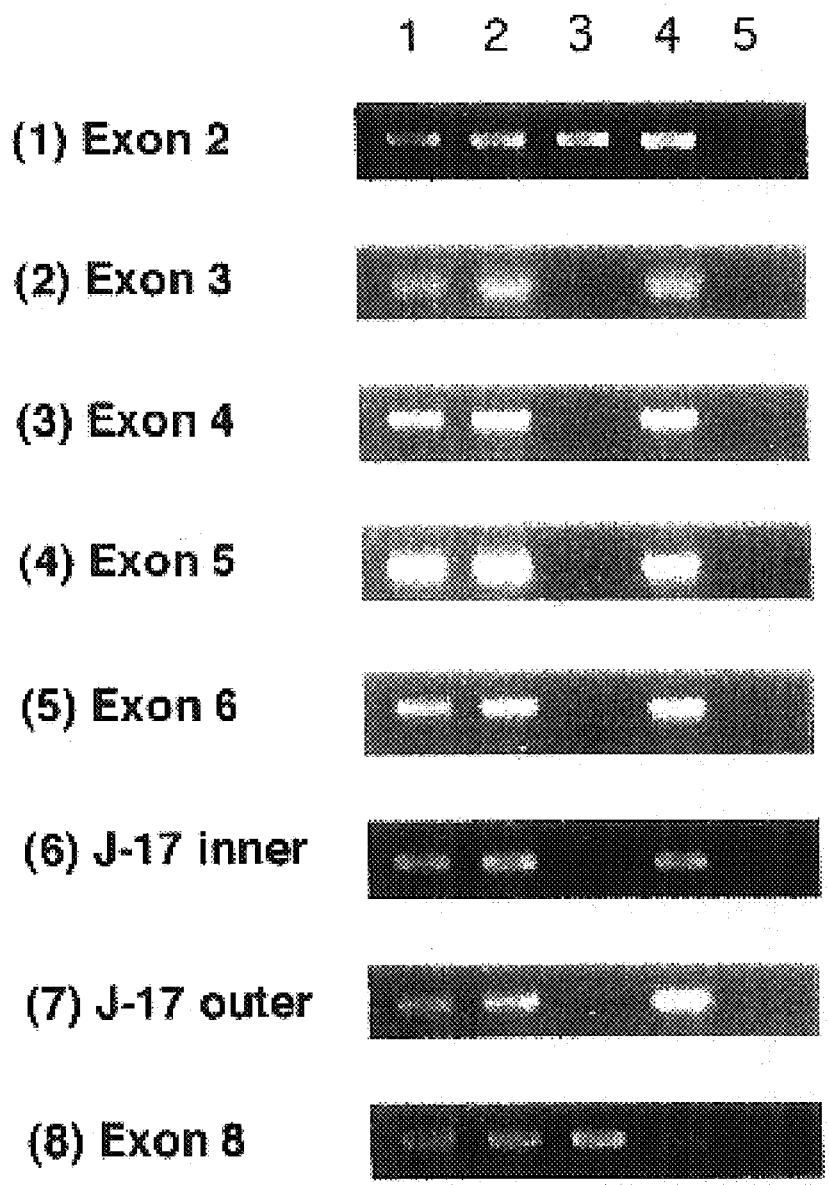
FIG. 3 is a diagram showing presence or absence of gene deletion in the family members including Parkinson's disease patient in FIG. 1.

Subsequently, base sequence of the intron adjacent to exon J-17 was determined based on the base sequence of exon J-17 by using a PCR primer to amplify exon J-17 itself (J-17 Inner), and BAC KB761D4 as template. Then, two sets of PCR primer (J-17 outer) were prepared to amplify the fragment including J-17 based on the thus-determined sequence of the intron. In this way, PCR amplification analysis was performed for the genomic DNA of the subjects shown in Example 1 (patient and the unaffected parents and brother). The result of analysis is shown in FIG. 3. It should be noted that FIG. 3 shows the result of Example 6 as well as the result of Example 2.

As shown in FIG. 3, no PCR product was detected from the genomic DNA of the patient (lane 3) whereas PCR product was detected from the normal genomic DNA of the father (lane 1), mother (lane 2) and brother (lane 4). This suggests that the patient has at least chromosomal deletion corresponding to exon J-17 of the inventive gene.

EXAMPLE 3

Screening of Inventive Gene from Normal Human cDNA Library

Next, screening of the inventive gene was performed using human cDNA library to isolate cDNAs which cover the full-length of the gene including J-17 together with full-length of its translation sequence. Specifically, cDNA libraries of normal human fetal brain and skeletal muscle were purchased from Clontech. J-17 fragment, which is part of exon of the inventive gene and was isolated in Example 2, was used as an initial probe, and insertion DNA fragment of positive clones isolated by initial screening using the initial probe were used as probes for secondary screening. As a result, seven cDNA clones [HFB 1, HFB3, HFB4, HFB5, SKM1, SKM3, and SKM8] shown in FIG. 4 were isolated. The insertion DNA fragments of positive clones were amplified with two set of vector-specific primer (F10inner: 5'-AGCCTGGTTAAGTCCAAGCTG-3' (SEQ ID NO: 5) and R10inner: 5'-GAAGGTCCCATTTTTCGTTTTC-3' (SEQ ID NO: 6)).

The thus amplified positive DNA fragment was sequenced directly according to primer walking method. Cycle sequencing was performed using the above-mentioned primers and a commercial kit [ABI PRISM labeling kits (manufactured by Perkin-Elmer)] and ABI model 377DNA sequencer (manufactured by Applied Biosystems) according to the manufacture's instruction manual.

Figure 4:
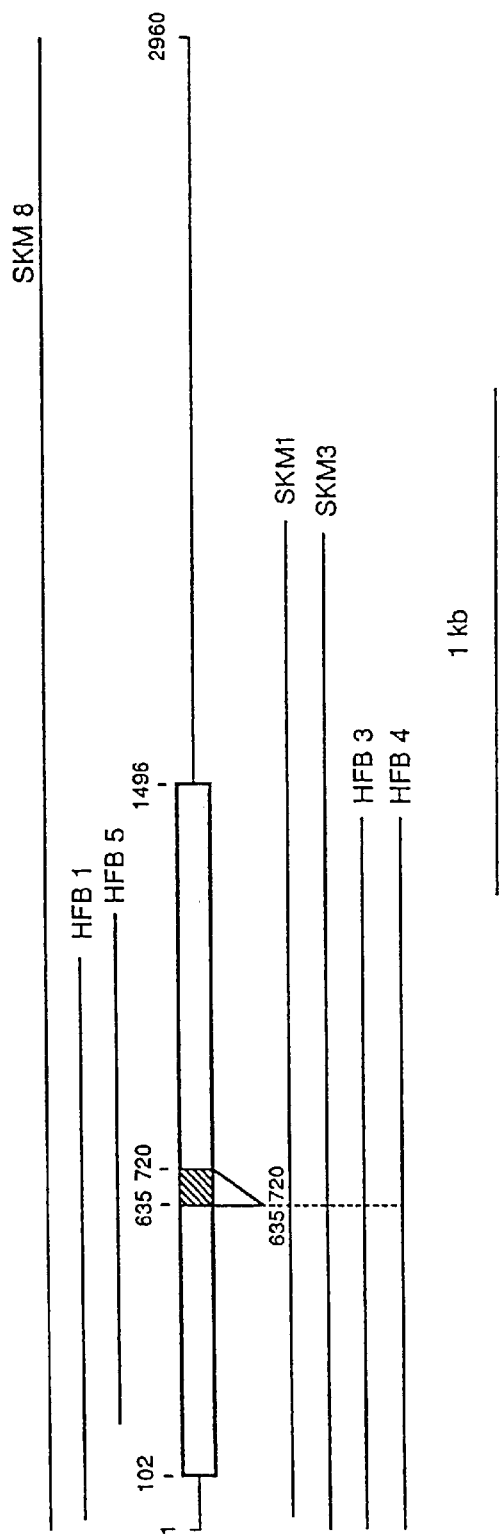
FIG. 4 is a diagram showing an alignment of six cDNA fragments and one full-length gene isolated in Example 3.

As a result, it was found that seven cDNAs had an piled relationship as shown in FIG. 4. The longest base sequence SKM8 has 2960 bp which includes a full-length of translation sequence which encodes a protein containing 1395 bp (nt102 to nt1496 or to nt1499 including stop codon), and 465 amino acids.

Also, it was found that four cDNA clones (HFB3, HFB4, SKM1, and SKM3) of seven cDNA lost 84 bp from nt636 to nt719. This implicates that there are at least two ways of splicing when mature mRNA grows from this inventive gene on genome by splicing.

Further, it was verified that the N-terminal portion (ranging from methionine-1 to arginine-72) of the protein consisting of 1 to 465 amino acid sequence which is encoded by the inventive gene has a moderate homology (content of the same amino acid: 33%) with ubiquitin as shown in FIG. 5.

Ubiquitin is known as a significant substance which removes a protein that has no longer been necessary in a cell, and involvement with various neurodegenerative diseases has also been pointed out. For instance, it has been known that paired helical filaments (PHFs) in Alzheimer's disease and Lewy bodies in Parkinson's disease are stained by an anti-polyubiquitin antibody. The mechanism is considered to act as follows. Ubiquitin is conjugated with various proteins and forms multi-ubiquitin chain by repeated conjugations, and induces to the proteasome pathway, finally to be metabolized.

Lysine residue-48 is known to be an essential element for ubiquitin-conjugate. Since lysine exists at position 48 in the protein, and the amino acid sequence at the vicinity of the target region (for instance, positions 44 to 48 and position 51) conforms with that of ubiquitin, it is suggested that the protein has ubiquitin-like function. Further, recent studies found some of conjugated proteins contain ubiquitin-like portion at the N-terminal portion thereof. The latter finding implies that the ubiquitin-like portion acts as a molecular chaperone.

Although homology with ubiquitin us observed at the N-terminal portion of this inventive protein as described above, homology with ubiquitin is seldom observed with respect to amino acid sequence at position 73 and thereafter. As another feature, the protein of this invention has amino acid sequence at the vicinity of the C-terminal portion (positions 418 to 449) containing a large number of cysteine residues: $Cys-X_2-Cys-X_9-Cys-X_1-His-X_2-Cys-X_4-Cys-X_4-Cys-X_2-Cys$ (SEQ ID NO: 7). This sequence is extremely similar to that of a ring-finger motif $(Cys-X_2-Cys-X_{(9-399)}-Cys-X_{(1-3)}-His-X_{(2-3)}-Cys-X_2-Cys-X_{(4-48)}-Cys-X_2-Cys)$ (SEQ ID NO: 8), a kind of sequence of a zinc-binding motif in a zinc-finger protein (a protein conjugate with zinc, and deeply involved in growth, differentiation, and generation of a cell). Accordingly, it is presumed that the protein of this invention is one of novel zinc-finger proteins.

Identification of each exon and sequencing of intron adjacent to each exon were performed according to Primer walking method (BEE procedure) using the above-obtained twenty five clones. As a result of analysis, exon 1 to 3, 5, 6, and 8–12 were mapped to either one of the twenty five BAC clones. Also, it was verified that J-17 corresponds to exon 7. BAC clones having genomic sequence including exon 4 were not, however, found in the twenty five BAC clones.

Another PCR primer to amplify exon 4 was prepared, and two new positive clones were obtained by PCR screening using a genome library supplied by Genome Systems Inc. Sequencing of each exon and intron adjacent to each exon was performed according to the aforementioned primer walking method with use of twenty seven BAC-DNA clones as template. The primers used in primer walking method were appropriately prepared based on cDNA sequence. BAC clones corresponding to the respective primers were separated according to oligonucleotide colony hybridization using primer itself as a probe. DNA sequencer was used for their sequencing.

As a result, the alignment of exon and intron of this inventive gene was made clear. It was verified that the gene of this invention has a very large spanning over 500 kb and consists of twelve exons intervening very large eleven introns. The intron sequence in the boundary region between exon and intron was described as above. Table 1 shows the whole base sequences in exon-intron boundaries.

TABLE 1

Intron - exon boundaries of Parkin gene

| | Exon | Intron | | Exon | |
|---|---|---|---|---|---|
| Exon 1 | ACCATGATAG | gtacgtgggt (SEQ ID NO:9)....ccttggtcag | TGTTTGTCAG | (SEQ ID NO:10) | Exon 2 |
| Exon 2 | GACTGTGCAG | gtgagtctcc (SEQ ID NO:11)....tcccaaacag | AATTGTGACC | (SEQ ID NO:12) | Exon 3 |
| Exon 3 | GGAAGTCCAG | gtaattggaa (SEQ ID NO:13)....tcttctccag | CAGGTAGATC | (SEQ ID NO:14) | Exon 4 |
| Exon 4 | CTTGACCCAG | gtaaggaaat (SEQ ID NO:15)....tttcccaaag | GGTCCATCTT | (SEQ ID NO:16) | Exon 5 |
| Exon 5 | GACTAGTGCA | gtaagtacct (SEQ ID NO:17)....tttctttcag | GAATTTTTCT | (SEQ ID NO:18) | Exon 6 |
| Exon 6 | CAGACGTCAG | gtaaggatct (SEQ ID NO:19)....ctctctgcag | GAGCCCCGTC | (SEQ ID NO:20) | Exon 7 |
| Exon 7 | CCTTGTGTGG | gtaagtctag (SEQ ID NO:21)....tttccaacag | CTGGCTGTCC | (SEQ ID NO:22) | Exon 8 |
| Exon 8 | AGAAGAGCAG | gtgagtgagc (SEQ ID NO:23)....ggttttgcag | TACAACCGGT | (SEQ ID NO:24) | Exon 9 |
| Exon 9 | GGGCTGTGGG | gtgagtactg (SEQ ID NO:25)....tcttttgcag | TTTGCCTTCT | (SEQ ID NO:26) | Exon 10 |
| Exon 10 | AACTACTCAG | gtacagaatg (SEQ ID NO:27)....gtttcoccag | GCCTACAGAG | (SEQ ID NO:28) | Exon 11 |
| Exon 11 | GAAAAAAATG | gtgagtctgt (SEQ ID NO:29)....cccccaacag | GAGGCTGCAT | (SEQ ID NO:30) | Exon 12 |

EXAMPLE 4

Screening of the Inventive Genomic Gene From Genome Library

As mentioned above, only exon (J-17) was found in two positive genomic clones (KB761D4 and KB430C4) which were obtained in Example 2. In this Example, by the purpose of obtaining a genimic fragment containing other exon(s), BAC clone screening was performed by hybridization of DNA from a genome library consisting of 95,232 clones (Keio human BAC library), using SKM8 clone which has the largest size among the positive clones obtained from the aforementioned cDNA library, as a probe. As a result, 24 new positive clones were obtained.

In addition, a PCR primer for amplifying exon 1, which corresponds to the N-terminal portion of the cNDA base sequence was prepared, screening of BAC library according to PCR amplification was performed, and another new positive clone was obtained.

EXAMPLE 5

Determination of Base Sequence of Exonic Part on Genomic DNA

Next, the base sequence of exon part obtained in Example 4 was amplified to verify whether the base sequence of the part conforms with that of the corresponding part of cDNA. Specifically, fourteen sets of primers were prepared based on flanking intron sequence at the 5'-terminus and 3'-terminus of each exon (part of the primer was prepared based on partial sequence of exon), and PCR amplification was performed with use of DNAs which have been prepared by the standard procedure with use of normal human peripheral blood leukocytes as template. For reference, Table 2 shows the base sequences of the fourteen primer sets used in this Example.

TABLE 2

Primer sequences and sizes of expected PCR products

| | Exon primer | | Forward (5'–3") | | Reverse (5'–3') | | product size (bp) |
|---|---|---|---|---|---|---|---|
| 1 | Ex 1 | | GCGCGGCTGGCGCCGCTGCGCGCA | (SEQ ID NO:31) | GCGGCGCAGAGAGGCTGTAC | (SEQ ID NO:32) | 112 |
| 2 | Ex 2 | | ATGTTTGCTATCACCATTTAAGGG | (SEQ ID NO:33) | AGATTGGCAGCGCAGGCGGCATG | (SEQ ID NO:34) | 308 |
| 3 | Ex 3 | | ACATGTCACTTTTGCTTCCCT | (SEQ ID NO:35) | AGGCCATGCTCCATGCAGACTGC | (SEQ ID NO:36) | 427 |
| 4 | Ex 4 | inner | AGGTAGATCAATCTACAACAGCT | (SEQ ID NO:37) | CTGGGTCAAGGTGAGCGTTGCCTGC | (SEQ ID NO:38) | 121 |
| 4 | Ex 4 | outer | ACAAGCTTTTAAAGAGTTTCTTGT | (SEQ ID NO:39) | AGGCAATGTGTTAGTACACA | (SEQ ID NO:40) | 261 |
| 5 | Ex 5 | | ACATGTCTTAAGGAGTACATTT | (SEQ ID NO:41) | TCTCTAATTTCCTGGCAAACAGTG | (SEQ ID NO:42) | 227 |
| 6 | Ex 6 | | AGAGATTGTTTACTGTGGAAACA | (SEQ ID NO:43) | GAGTGATGCTATTTTTAGATCCT | (SEQ ID NO:44) | 268 |
| 7 | J-17 | inner | GAGCCCCGTCCTGGTTTTCC | (SEQ ID NO:45) | CCACACAAGGCAGGGAGTAGCCAA | (SEQ ID NO:46) | 137 |
| 7 | J-17 | outer | TGCCTTTCCACACTGACAGGTACT | (SEQ ID NO:47) | TCTGTTCTTCATTAGCATTAGAGA | (SEQ ID NO:48) | 239 |
| 8 | Ex 8 | | TGATAGTCATAACTGTGTGTAAG | (SEQ ID NO:49) | ACTGTCTCATTAGCGTCTATCTT | (SEQ ID NO:50) | 206 |
| 9 | Ex 9 | | GGGTGAAATTTGCAGTCAGT | (SEQ ID NO:51) | AATATAATCCCAGCCCATGTGCA | (SEQ ID NO:52) | 278 |
| 10 | Ex 10 | | ATTGCCAAATGCAACCTAATGTC | (SEQ ID NO:53) | TTGGAGGAATGAGTAGGGCATT | (SEQ ID NO:54) | 165 |
| 11 | Ex 11 | | ACAGGGAACATAAACTCTGATCC | (SEQ ID NO:55) | CAACACACCAGGCACCTTCAGA | (SEQ ID NO:56) | 303 |
| 12 | Ex 12 | | GTTTGGGAATGCGTGTTTT | (SEQ ID NO:57) | AGAATTAGAAAATGAAGGTAGACA | (SEQ ID NO:58) | 255 |

The above PCR amplification was carried out in the following manner. In this Example, 10 ml-reactions were prepared, each of which contained 100 ng DNA, 1×PCR buffer [50 mM Tris-HCl (pH 9.2 at 25° C.), 14 mM $(NH_4)_2SO_4$, 1.75 mM $MgCl_2$], 350 μM each dNTP, 0.5 μM each primer and 0.35 U Expand Long Taq polymerase (Boerhinger Manheim). PCR conditions were at 94° C. for 30 sec., 50–53° C. for 30 sec., 68° C. for 30 sec. to 1 min. and repeated 35 cycles.

Base sequence of each DNA fragment that has been amplified by the above PCR was determined using appropriate PCR primers and a commercial kit. The result of sequencing is shown in Table 2.

As shown in Table 2, it was verified that the base sequence amplified according to the PCR using the aforementioned primers conforms with that of the corresponding part of cDNA.

EXAMPLE 6

Partial Deletion of Inventive Gene in Juvenile Parkinson's Disease Patient (Case 1)

In this Example, abnormality of the inventive gene was examined using the juvenile Parkinson's disease patient and family members in Example 1.

Specifically, genomic DNAs were prepared from the leukocytes of the subjects, and PCR amplification was carried out using the genomic DNAs as template and primer sets consisting of forward (5'-3') and reverse (5'-3') of exon 2, exon 3, J-17 inner, J-17 outer, and exon 8 among the primer sets listed in Table 2. The result of analysis is shown in FIG. 3.

As seen from FIG. 3, in the case where the genomic DNAs of father (lane 1), mother (lane 2), and brother (lane 4) of the Parkinson's disease patient were used as template, the sequence corresponding to each exon was amplified. This result verifies that the genomic DNAs of these family members do not have deletion or significant mutation. On the other hand, in the case where the genomic DNA of the Parkinson's disease patient (lane 3) was used as template, no amplification of the base sequence of the genomic DNA corresponding to exons 3, 4, 5, 6, 7 was found. This result clarified that the genomic gene of the patient has a deletion of long base sequence corresponding to exons 3 to 7.

Figure 6:
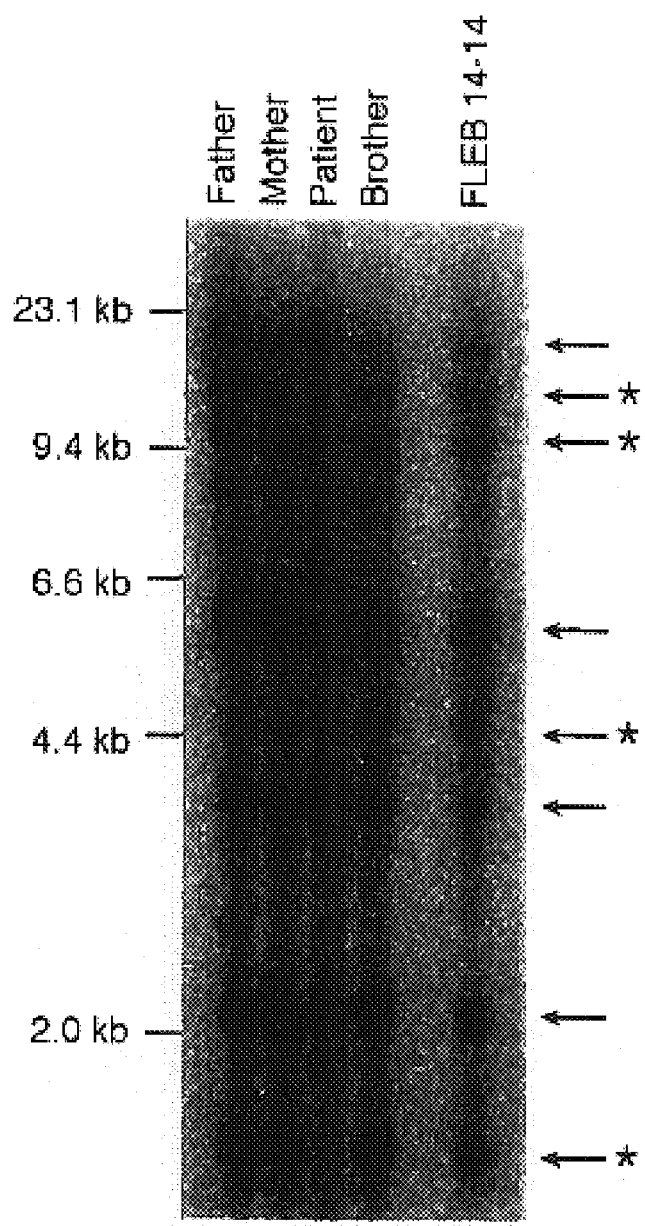
FIG. 6 is a diagram showing the result of gel electrophoresis of EcoRI digest of genomic DNA fragments with respect to the family members including Parkinson's disease patient in FIG. 1.

Furthermore, the genomic DNAs of the subjects were digested with EcoRI, electrophoresed, and blotted onto nylon membrane by Southern blot analysis, and P32-labeling of SKM8 cDNA probe was performed by Southern blot hybridization. As a result, as shown in FIG. 6, whereas at least eight EcoRI fragments were found in the parents and brother of the patient, only four fragments were found in the patient (in FIG. 6, asterisk denotes the four EcoRI fragment that, were not detected in the patient). This result also verifies that the genomic gene of the patient has deletion or mutation at a certain part thereof.

EXAMPLE 7

Partial Deletion of Inventive Gene in Juvenile Parkinson's Disease Patient (Case 2)

As can be seen from Example 6, it is obvious that juvenile Parkinson's disease patients have deletion or the like in the inventive gene. The above example strongly implicates that deletion or the like of the inventive gene is responsible for juvenile Parkinson's disease. To further verify this, similar experiments were conducted with respect to another unrelated family members to those in Example 6.

Figure 7:
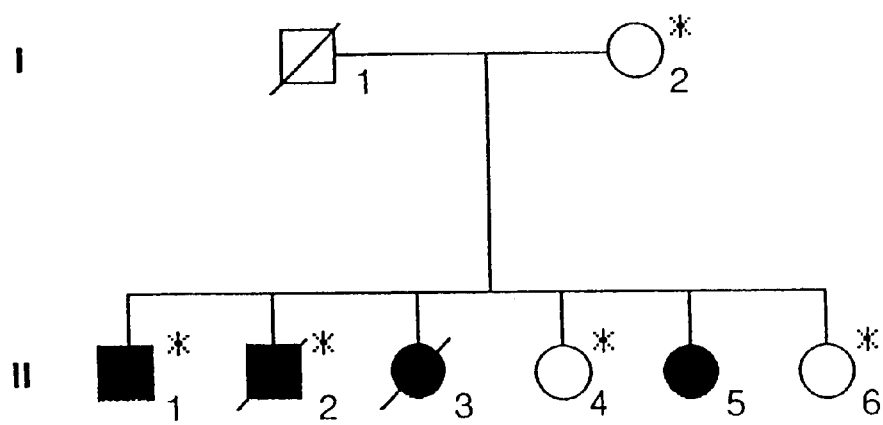
FIG. 7 is a diagram showing the pedigree of family members including Parkinson's disease patients in Example 7.

Specifically, genome analysis was carried out with respect to the family members including juvenile Parkinson's disease patients of the pedigree in FIG. 7. Whereas two siblings out of six are unaffected, the other four siblings are all juvenile Parkinson's disease patients. PCR analysis was performed in accordance with the procedure in Example 5 using primers corresponding to respective exons with use of the genomic DNAs of the members marked with asterisk (namely, unaffected mother, two unaffected brothers, and two affected sisters) as template. The result of analysis is shown in FIG. 8.

Figure 8:
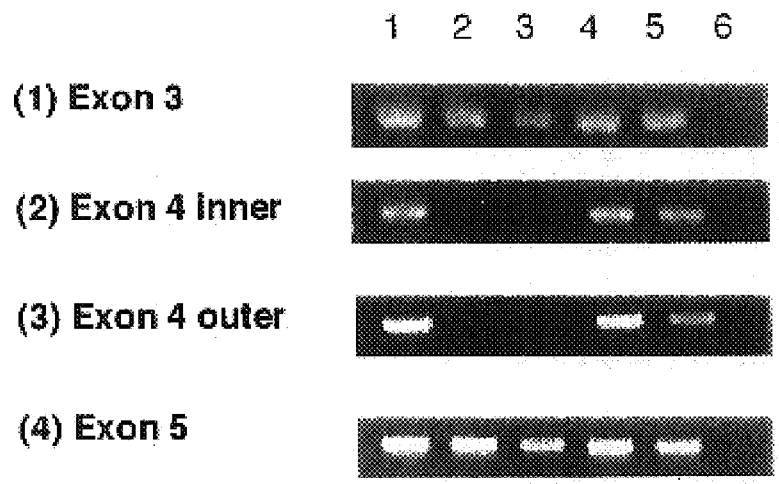
FIG. 8 is a diagram showing presence or absence of gene deletion with respect to the family members including Parkinson's disease patient in FIG. 7.

As can be seen from FIG. 8, whereas both of the genomic DNAs of the two patients (lanes 2 and 3) in this Example show deletion of exon 4, none of the genomic DNAs of the other subjects (unaffected mother (lane 1) and two unaffected sisters (lane 5 and 6)) have deletion.

Furthermore, mRNA was extracted from the brain tissue of one of the patients according to the standard AGPC procedure. Total 1 mg of mRNA was primed at 50° C. for 30 min. using Titan™ one tube RT-PCR System kit (Boehringer Manheim), and the reaction mixture was directly used for PCR with forward primer (nt 351 to nt 371 of SEQ ID. No. 1) 5'-GGAGGCGACGACCCCAGAAAC-3' and reverse primer (nt 963 to nt 983 of SEQ ID. No. 1) 5'-GGGACAGCCAGCCACACAAGG-3' (SEQ ID NO:70). PCR was performed at 94° C. for 30 sec., 56° C. for 30 sec., 68° C. for 1 min. and repeated 45 cycles. cDNA sequence of PCR products obtained by the above procedure was analyzed, and the result of analysis is shown in FIG. 9.

Figure 9:
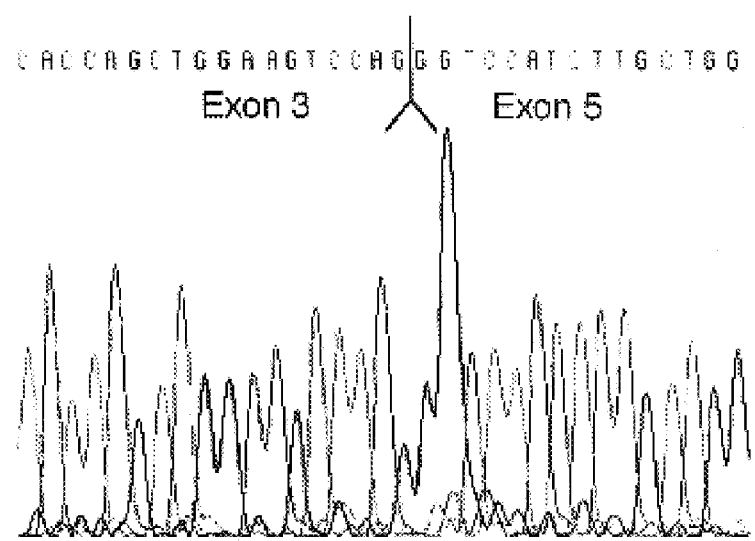
FIG. 9 is a diagram showing the sequence of a cDNA fragment (SEQ ID NO:63) of the Parkinson's disease patient in FIG. 7, obtained by Example 7.

As seen from FIG. 9, mRNA of the patient shows complete deletion of exon 4, exon 3 is contiguous to exon 5 directly by skipping exon 4. Consequently, it was verified that the juvenile Parkinson's disease patients of two unrelated family members have deletion of exon in the inventive gene and that deletion of the inventive gene is responsible for juvenile Parkinson's disease.

The results of FIGS. 10 to 11 show that mRNA was particularly richly expressed in the tissue of brain, heart, testis and skeletal muscle although mRNA of 4.5 kb including poly A-tail was detected in all the tissues examined in this Example. It was further verified that expression was particularly remarkable in the cerebral cortex and frontal lobe although the expression was detected in every section of the brain.

EXAMPLE 9

Partial Deletion of Inventive Gene in Juvenile Parkinson's Disease Patient (Case 3)

Figure 12:
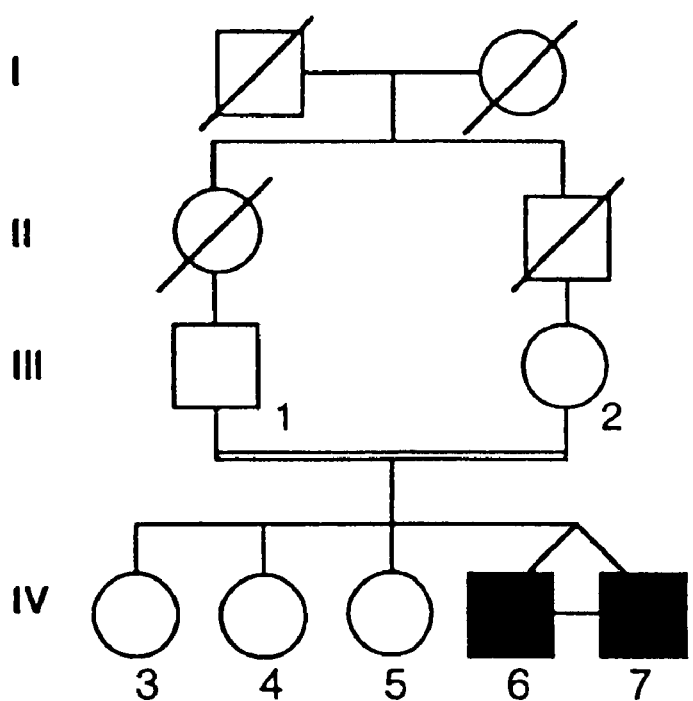
FIG. 12 is a diagram showing the pedigree of family members including Parkinson's disease patients in Example 9.

FIG. 12 shows the pedigree of family members including Parkinson's disease patients in Example 9. In this Example, genomic DNAs were prepared from leukocytes of the subjects marked with numerals 1 to 7 in FIG. 12 (namely, unaffected parents, three unaffected sisters, and two affected brothers) and used as template. PCR amplification was performed using oligonucleotide primer pairs shown in Table 3.

TABLE 3

Primer sequences and sizes of PCR products

| Exon | primer | Forward (5'–3") | | Reverse (5'–3') | | product size (bp) |
|---|---|---|---|---|---|---|
| 1 | Ex 1 | GCGCGGCTGGCGCCGCTGCGCGCA | (SEQ ID NO:31) | GCGGCGCAGAGAGGCTGTAC | (SEQ ID NO:32) | 112 |
| 2 | Ex 2 | ATGTTTGCTATCACCATTTAAGGG | (SEQ ID NO:33) | AGATTGGCAGCGCAGGCGGCATG | (SEQ ID NO:34) | 308 |
| 3 | Ex 3 | ACATGTCACTTTTGCTTCCCT | (SEQ ID NO:35) | AGGCCATGCTCCATGCAGACTGC | (SEQ ID NO:36) | 427 |
| 4 | Ex 4 | ACAAGCTTTTAAAGAGTTTCTTGT | (SEQ ID NO:39) | AGGCAATGTGTTAGTACACA | (SEQ ID NO:40) | 261 |
| 5 | Ex 5 | ACATGTCTTAAGGAGTACATTT | (SEQ ID NO:41) | TCTCTAATTTCCTGGCAAACAGTG | (SEQ ID NO:42) | 227 |
| 6 | Ex 6 | AGAGATTGTTTACTGTGGAAACA | (SEQ ID NO:43) | GAGTGATGCTATTTTTAGATCCT | (SEQ ID NO:44) | 268 |
| 7 | Ex 7 | TGCCTTTCCACACACTGACAGGTACT | (SEQ ID NO:47) | TCTGTTCTTCATTAGCATTAGAGA | (SEQ ID NO:48) | 239 |
| 8 | Ex 8 | TGATAGTCATAACTGTGTGTAAG | (SEQ ID NO:49) | ACTGTCTCATTAGCGTCTATCTT | (SEQ ID NO:50) | 206 |
| 9 | Ex 9 | GGGTGAAATTTGCAGTCAGT | (SEQ ID NO:51) | AATATAATCCCAGCCCATGTGCA | (SEQ ID NO:52) | 278 |
| 10 | Ex 10 | ATTGCCAAATGCAACCTMTGTC | (SEQ ID NO:59) | TTGGAGGAATGAGTAGGGCATT | (SEQ ID NO:54) | 165 |
| 11 | Ex 11 | ACAGGGAACATAAACTCTGATCC | (SEQ ID NO:55) | CAACACACCAGGCACCTTCAGA | (SEQ ID NO:56) | 303 |
| 12 | Ex 12 | GTTTGGGAATGCGTGTTTT | (SEQ ID NO:57) | AGAATTAGAAAATGAAGGTAGACA | (SEQ ID NO:58) | 255 |

EXAMPLE 8

Inventive Gene mRNA Expression in Various Tissues

In this Example, Northern blot analysis was carried out using the genomic fragment J-17 in order to examine how widely mRNA[Poly(A)+] of the inventive gene is expressed in various human tissues.

Figure 10A:
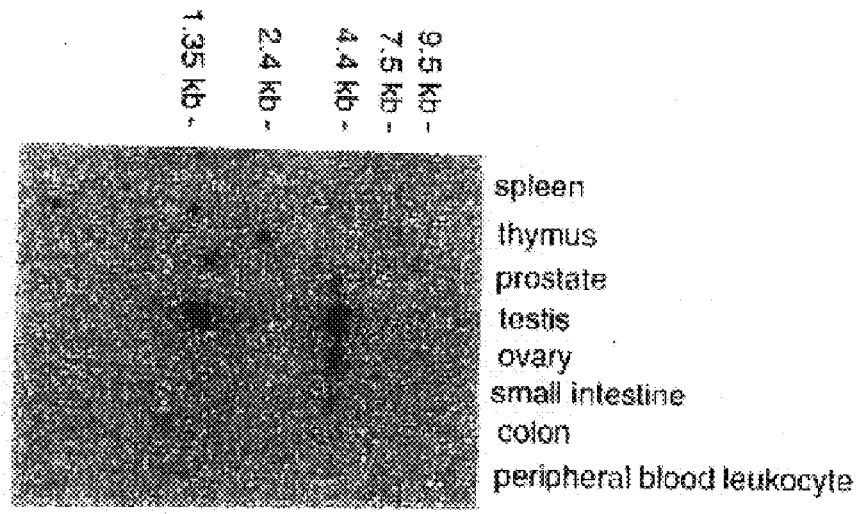
FIGS. 10A–10C are diagrams showing mRNAs of the inventive gene that are expressed in various human tissues.
Figure 10B:
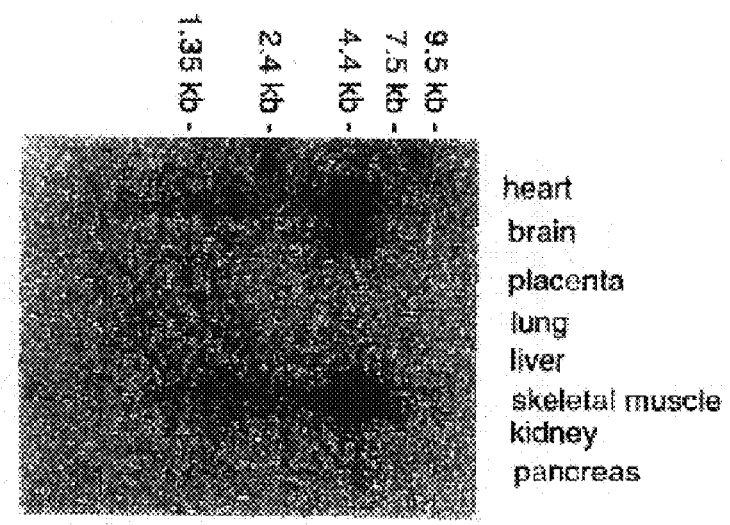
Figure 10C:
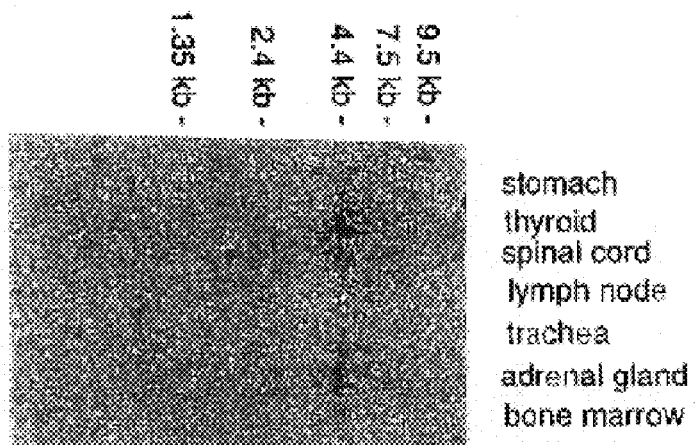
Figure 11A:
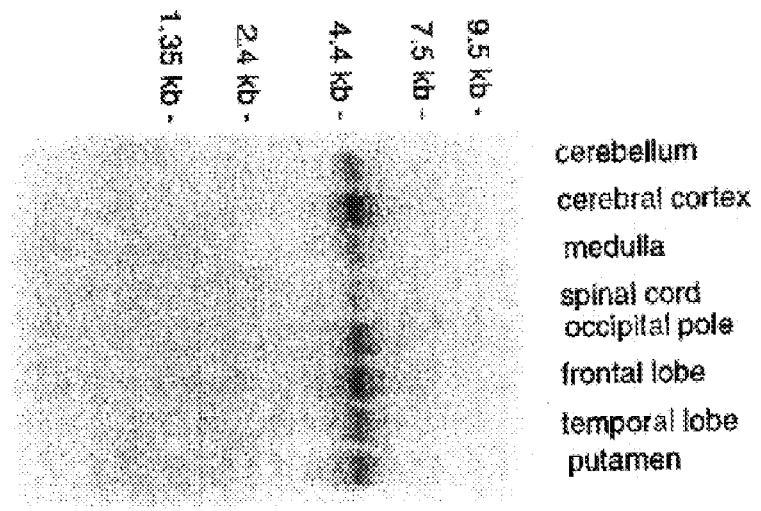
FIGS. 11A–11B are diagrams showing mRNAs of the inventive gene that are is expressed in various human tissues.
Figure 11B:
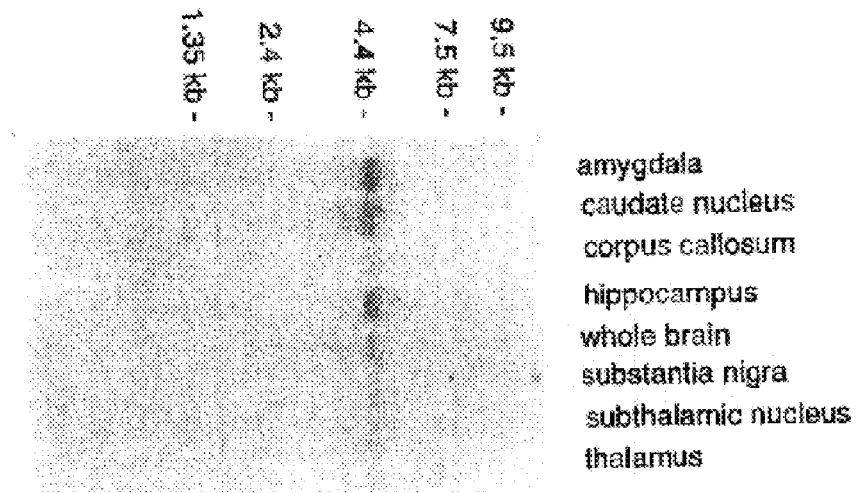

Specifically, Northern blots of various human tissues were purchased from Clontech, and northern blotting was carried out according to the provided instruction manual with use of J-17 corresponding to exon 4 of the inventive gene, as a probe. The result of analysis is shown in FIGS. 10 to 11. It should be noted that tissues in FIG. 10A are, from left to right in the order, are spleen, thymus, prostate, testis, ovary, small intestine, colon, and peripheral blood leukocyte; those in FIG. 10B are, from left to right in the order, heart, brain, placenta, lung, liver, skeletal muscle, kidney, and pancreas; those in FIG. 10C are, from left to right in the order, stomach, thyroid, spinal cord, lymph node, trachea, adrenal gland, and bone marrow; those in FIG. 11A are, from left to right in the order, cerebellum, cerebral cortex, medulla, spinal cord, occipital pole, frontal lobe, temporal lobe, and putamen; and those in FIG. 11B are, from left to right in the order, amygdala, caudate nucleus, corpus callosum, hippocampus, whole brain, substantia nigra, subthalamic nucleus, and thalamus.

All the reactions were carried out according to the following procedure. Prepared was a 25 µl reaction mixture containing 50 mM KCl, 10 mM Tris (pH 8.3), 1.5 mM MgCl$_2$, 0.02% gelatin with primers, 10 nmol of each dNTP, and 2.5 units of AmpliTaq Gold DNA polymerase (Perkin-Elmer Applied Biosystems Division). Initial denaturation at 94° C. for 10 min. was followed by 40 cycles of 94° C. for 30 sec., 55° C. for 30 sec., and 72° C. for 45 sec., and then a final extension at 72° C. for 10 min. The PCR products were visualized on ethidium bromide-stained 2% agarose gels and the presence or absence of the target exon(s) was detected. The result is shown in FIG. 13.

Figure 13:
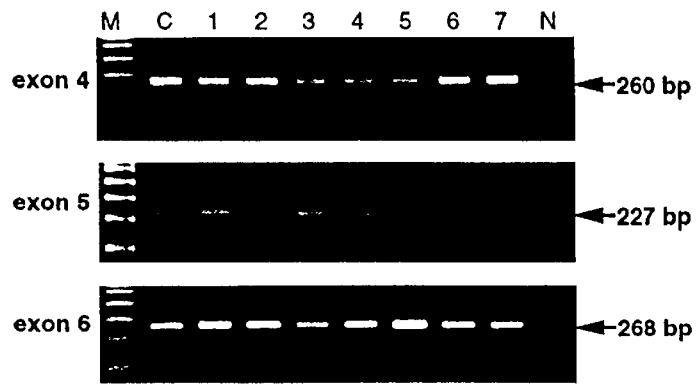
FIG. 13 is a diagram showing presence or absence of gene deletion in the family members including Parkinson's disease patient in FIG. 12.

As seen in FIG. 13, in the case where DNA of the two Parkinson's disease patients (lanes 6, 7) was used as template, no amplification of the regions corresponding to exon 5 was detected.

Figure 14:
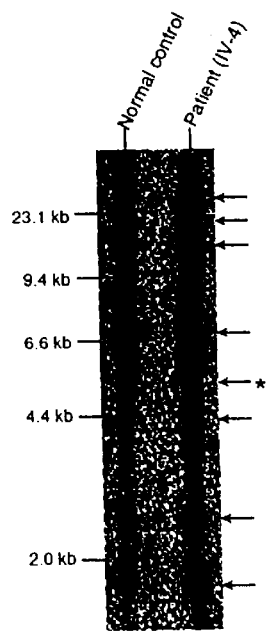
FIG. 14 is a diagram showing the result of gel electrophoresis of EcoRI digest of genomic DNA fragments with respect to the family members including Parkinson's disease patient in FIG. 12.

A further experiment was carried out. The genomic DNA of the Parkinson's disease patient (marked with numeral 6 in FIG. 12) and of his father was digested with EcoRI, electrophoresed, and blotted onto nylon membrane by Southern blotting. Then, P32-labeling of SKM8 DNA probe was subjected to Southern blot hybridization. The result of this analysis is shown in FIG. 14. As can be seen from FIG. 14, whereas at least eight EcoRI fragments were detected in the father, only seven EcoRI fragments were detected in the patient (in FIG. 14, asterisk mark denotes the undetected EcoRI fragment). This analysis verifies that the genomic gene of the Parkinson's disease patient has deletion or mutation in a specific regions of the inventive gene.

EXAMPLE 10

Partial Deletion of Inventive Gene in Juvenile Parkinson's Disease Patient (Case 4)

Figure 15:
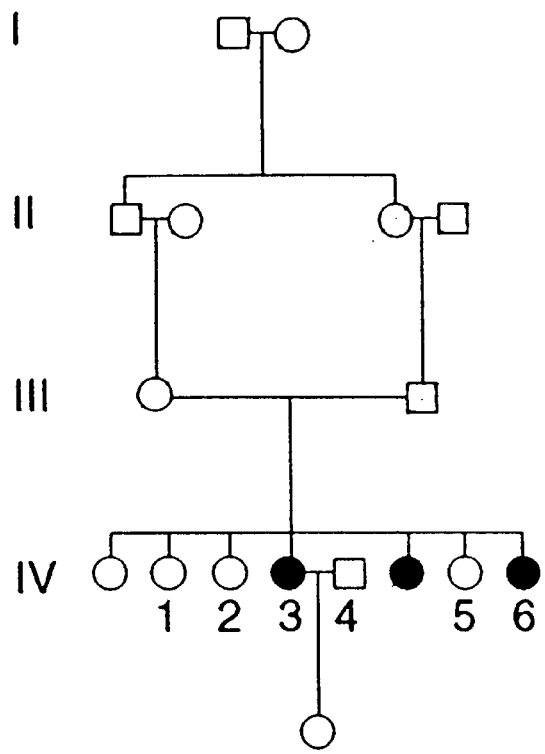
FIG. 15 is a diagram showing the pedigree of family members including Parkinson's disease patients in Example 10.

Another experiment was carried out in accordance with the procedure in Example 9 except that unrelated another family members to those in Example 9 were examined. Specifically, genomic analysis was carried out for the family members including juvenile Parkinson's disease patients of the pedigree shown in FIG. 15. Four sisters out of seven are unaffected, but the other three sisters have juvenile Parkinson's disease. PCR analysis was performed in accordance with the procedure in Example 9 using primers corresponding to respective exons with use of the genomic DNAs of the subjects marked with numerals 1 to 6 in FIG. 15, as template. The result of analysis is shown in FIG. 16.

Figure 16:
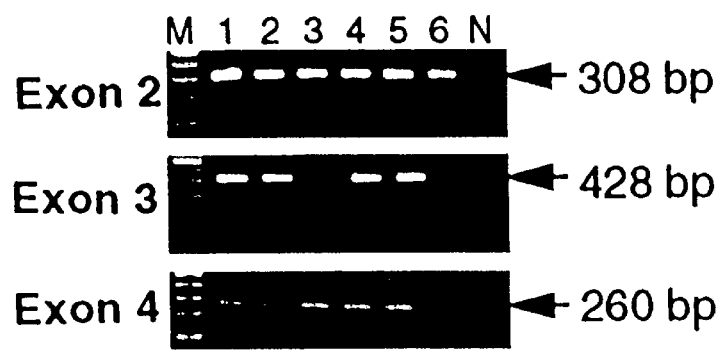
FIG. 16 is a diagram showing presence or absence of gene deletion with respect to the family members including Parkinson's disease patient in FIG. 15.

As shown in FIG. 16, in the case where the DNAs of the Parkinson's disease patients (lane 3 and 6) were used as template, no amplification was found with respect to the base sequence of the regions corresponding to exon 3.

EXAMPLE 11

Partial Deletion of Inventive Gene in Juvenile Parkinson's Disease Patient (Case 5)

Figure 17:
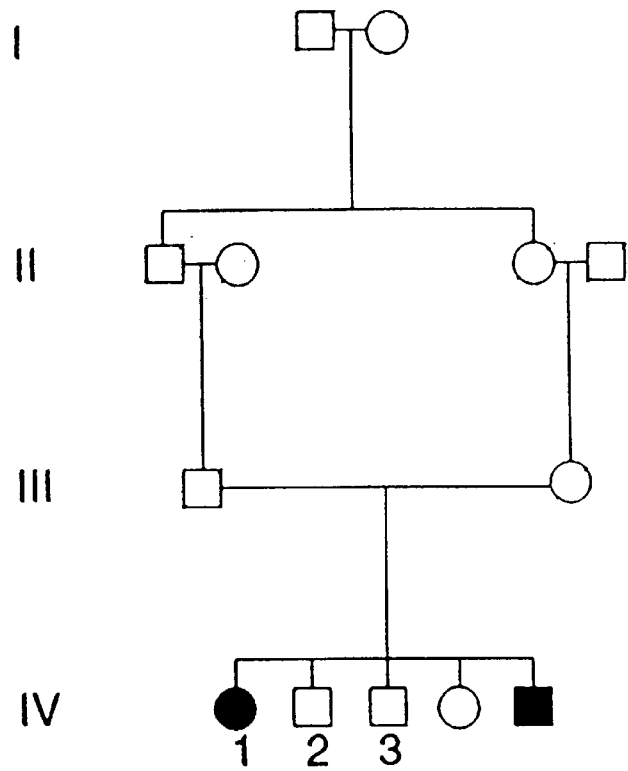
FIG. 17 is a diagram showing the pedigree of family members including Parkinson's disease patients in Example 11.

Another experiment was performed in accordance with the procedure in Example 9 except that unrelated family members to those in above Examples were examined. In this Example, genomic analysis was performed for the family members including juvenile Parkinson's disease patients of the pedigree shown in FIG. 17. Three siblings out of five are unaffected, but the other two siblings are juvenile Parkinson's disease patients. PCR analysis was performed in accordance with the procedure in Example 9 using primers corresponding to respective exons with use of the genomic DNAs of the subjects marked with numerals 1 to 3 in FIG. 17, as template. The result of analysis is shown in FIG. 18.

Figure 18:
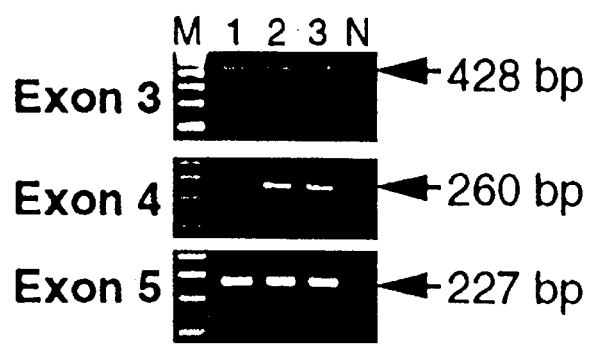
FIG. 18 is a diagram showing presence or absence of gene deletion with respect to the family members in FIG. 17.

As shown in FIG. 18, in the case where the DNA of the Parkinson's disease patient (lane 1) was used as template, no amplification was observed with respect to the base sequence of the regions corresponding to exon 4.

EXAMPLE 12

Partial Deletion of Inventive Gene in Juvenile Parkinson's Disease Patient (Case 6)

Figure 19:
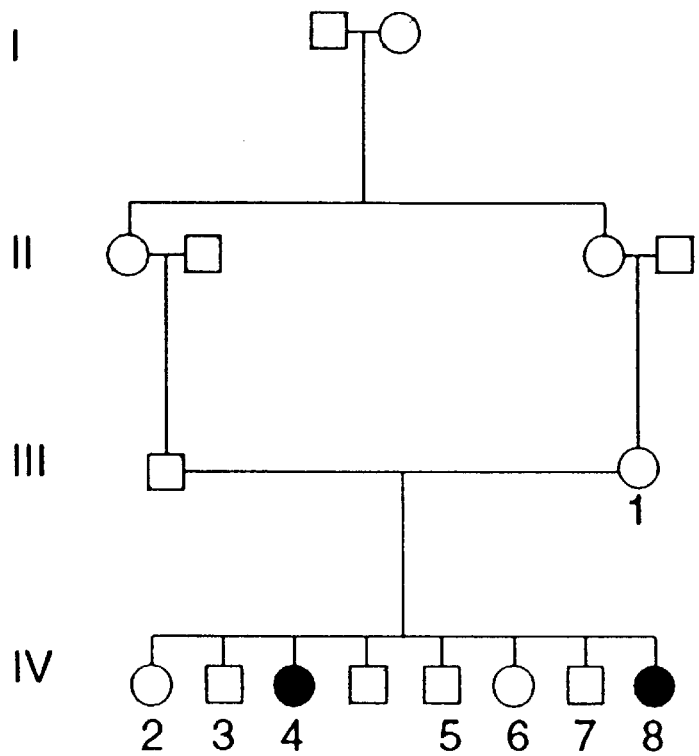
FIG. 19 is a diagram showing the pedigree of family members including Parkinson's disease patients in Example 12.

A further experiment was conducted in accordance with the procedure in Example 9 except that unrelated family members to those in above Examples were examined. Specifically, genomic analysis was performed for the family members including juvenile Parkinson's disease patients of the pedigree shown in FIG. 19. Parents and six siblings out of eight are unaffected, but the other two siblings are juvenile Parkinson's disease patients. PCR analysis was performed in accordance with the procedure in Example 9 using primers corresponding to respective exons with use of the genomic DNAs of the subjects marked with numerals 1 to 8 in FIG. 19, as template. The result of analysis is shown in FIG. 20.

Figure 20:
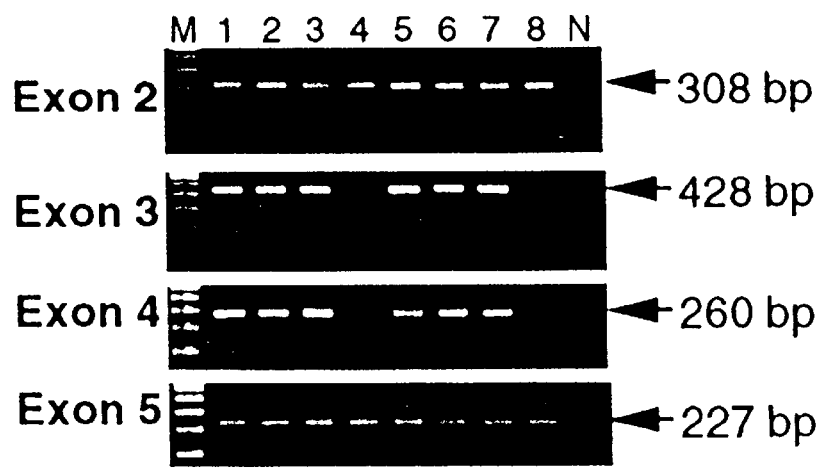
FIG. 20 is a diagram showing presence or absence of gene deletion with respect to the family members including Parkinson's disease patient in FIG. 19.

As shown in FIG. 20, in the case where the DNA of the Parkinson's disease patients (lane 4 and 8) were used as template, no amplification was observed with respect to the base sequence of the DNAs corresponding to exon 3 and exon 4.

EXAMPLE 13

Partial Deletion of Inventive Gene in Juvenile Parkinson's Disease Patient (Case 7)

Figure 21:
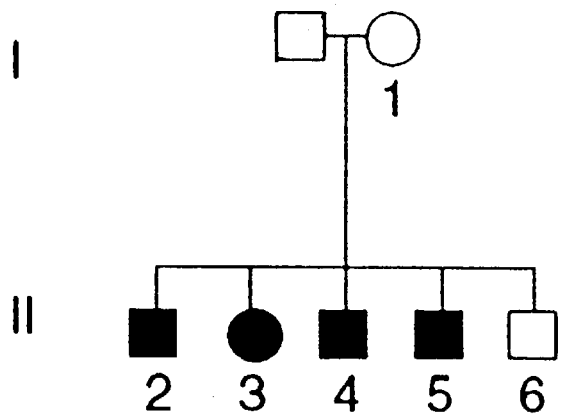
FIG. 21 is a diagram showing the pedigree of family members including Parkinson's disease patients in Example 13.

Another experiment was conducted in accordance with the procedure in Example 9 except that unrelated family members to those in the above Examples were examined. Specifically, genomic analysis was performed for the family members including juvenile Parkinson's disease patients of the pedigree shown in FIG. 21. Parents and one brother out of five siblings are unaffected, but the other four siblings are juvenile Parkinson's disease patients. PCR analysis was performed in accordance with the procedure in Example 9 using primers corresponding to respective exons with use of the genomic DNAs of the subjects marked with numerals 1 to 6 in FIG. 21, as template. The result of analysis is shown in FIG. 22.

Figure 22:
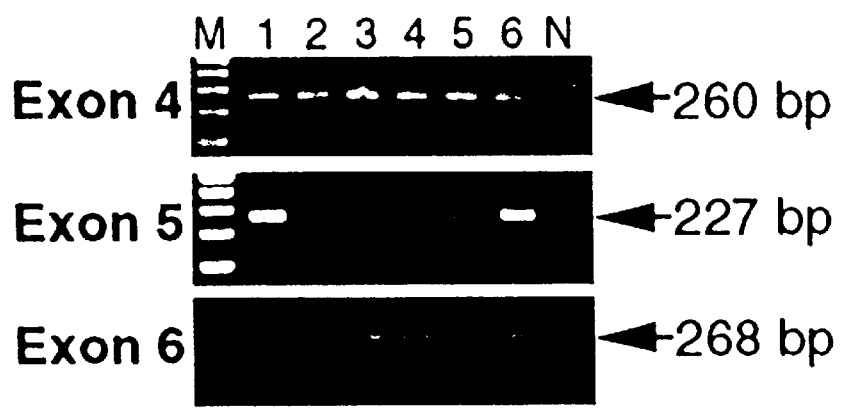
FIG. 22 is a diagram showing presence or absence of gene deletion with respect to the family members including Parkinson's disease patient in FIG. 21.

As shown in FIG. 22, in the case where the DNA of the Parkinson's disease patients (lane 2 to 6) were used as template, no amplification was observed with respect to the base sequence of the regions corresponding to exon 5.

EXAMPLE 14

Identification of Homozygous One-base Deletion in Exon 5

Figure 23:
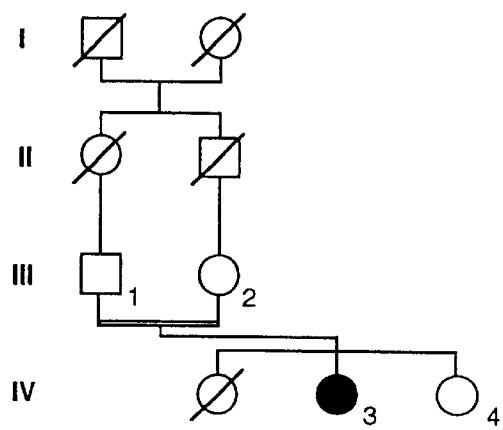
FIG. 23 is a diagram showing the pedigree of family members including Parkinson's disease patient in Example 14.

Screening was performed to determine deletion, insertion or point mutation according to direct sequencing PCR for one patient each from the family members of pedigree shown in FIG. 23 etc. PCR was performed with chimera primers that were specific to oligonucleotide primer sequences and had the sequences of the standard sequencing primers (M13 universal and reverse primers) at their 5'-ends, respectively. Excess primers and dNTPs were removed from the PCR products with an Ultrafree-MC centrifugal filter (Millipore). The purified PCR products were sequenced by the dideoxy chain termination method with an Applied Biosystems 373A DNA sequencer.

Figure 24:
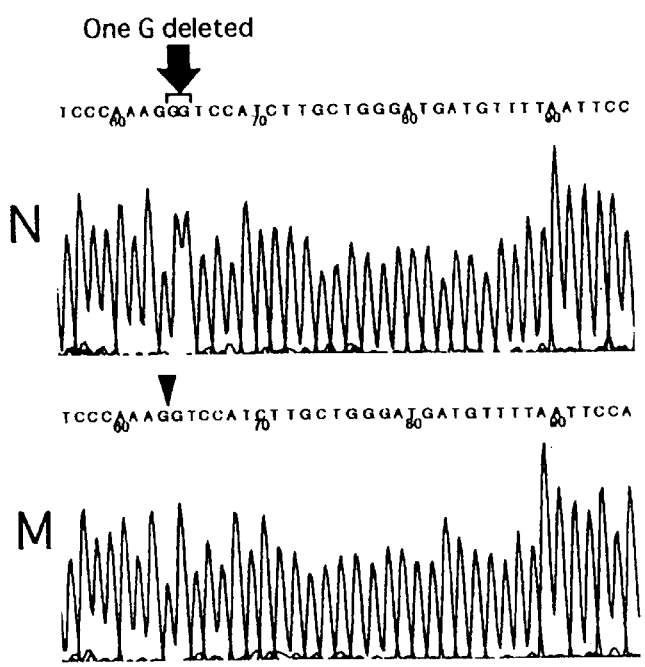
FIG. 24 is a chromatogram showing the result of direct sequencing of PCR products from exon 5 of a wild allele (SEQ ID NO:64) and a mutant allele (SEQ ID NO:65).

As a result of screening, one-base deletion in exon 5 was identified among the patients (see FIG. 24). In FIG. 24, the upper section (N) represents the result of direct sequencing of the PCR products from exon 5 of a wild allele, and the lower section (M) represents the result of direct sequencing of the PCR products from exon 5 of a mutant allele.

Figures 25, 26:
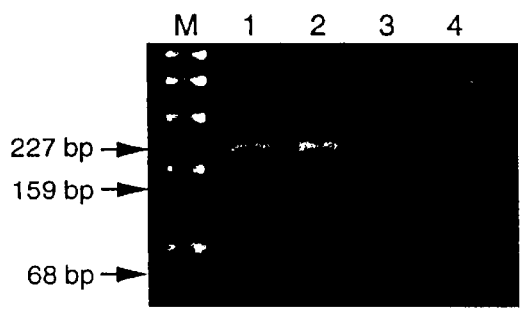
FIG. 25 is a diagram showing DNA (SEQ ID NO:66) and amino acid (SEQ ID NO:67) sequences of a wild-type (W) parkin gene, and predicted DNA (SEQ ID NO:68) and amino acid (SEQ ID NO:69) sequences of a mutant (M) parkin molecule having one-base deletion.
FIG. 26 is a diagram showing the result of NlaIV restriction site analysis of PCR products in Example 14.

More specifically, the one-base deletion removed one guanosine from the sequence -GGT- (codon 179), causing a frameshift that resulted in an intermediate stop codon at amino acid position 187. The nucleotide and predicted amino acid sequences are shown in FIG. 25. In FIG. 25, "Normal" section shows DNA and amino acid sequences of a wild-type allele, and "Mutant" section shows DNA and amino acid sequences of a mutant allele with one-base deletion, respectively. This one-base deletion was not detected in the normal subjects.

Next, to verify the one-base deletion in the patient (marked with numeral 3) of the pedigree shown in FIG. 23 and to identify the genotypes of her parents (marked with numerals 1 and 2) and her unaffected sister (marked with numeral 4), NlaIV restriction site analysis was performed. In this analysis, exon 5 of the subjects was amplified by primer pairs in accordance with the aforementioned procedure, and their PCR products were digested with NlaIV (New England Biolabs Inc., Massachusetts). The PCR products were electrophoresed on 3% (2% Agarose/1% NuSieve Agarose) gel and visualized with ethidium bromide. The result is shown in FIG. 26. In FIG. 26, lane 1 shows the sequence of father, lane 2 shows that of mother, lane 3 shows that of the patient, and lane 4 shows that of the unaffected sister, respectively.

The wild-type allele can be detected as an NlaIV site in exon 5, and digestion with NlaIV produced two fragments (159 bp and 68 bp). On the other hand, the mutant allele having one-base deletion showed a single fragment of 227 bp. This restriction site analysis verified that the patient is mutant homozygote due to one-base deletion in exon 5 whereas her parents are wild-type heterozygotes, and her unaffected sister is wild-type homozygote. These results are consistent with the mode of autosomal recessive mode of inheritance.

EXAMPLE 15

Immunohistochemical and Immunofluorescence Analysis of Inventive Gene in Juvenile Parkinson's Disease Patients In order to elucidate the molecular mechanism of substantia nigra (SN) caused by mutation of the inventive gene (hereinafter, sometimes referred to as "Parkin"), localization of the protein of this invention in the brains of patients with autosomal recessive juvenile Parkinsonism (AR-JP), sporadic Parkinson's disease (PD) and normal control subjects was examined by using antibodies against the protein of this invention.

More specifically, cases of fifteen PD patients, three AR-JP patients, and eight control subjects were studied. Among AR-JP patients, case 1 and case 2 are sisters, and they had a deletion of exon 4 in the inventive gene, resulting in a truncated protein of 143 amino acids due to a stop codon generated by the frameshift 6 amino acids after codon 138. Case 3 of AR-JP patient was a 52 year-old female patient and she had a deletion of exon 3 which causes a premature termination at amino acid 96 due to the frameshift after amino acid 58.

Two kinds of rabbit polyclonal antibodies (M-73 and M-74), rabbit polyclonal antibody against α-synuclein, and mouse monoclonal antibody against polyubiquitin were used respectively in this Example.

First of all, immunohistochemical staining was conducted according to the following procedure. Formalin-fixed paraffin-embedded sections of the midbrain, frontal lobe cortex, and putamen of the subjects were treated with anti-Parkin M-74, anti-α-synuclein, or anti-polyubiquitin antibodies after appropriate dilution by a standard avidin-biotin complex method using 3',3'-diaminobenzidine for visualization. Double-immunofluorescence was performed with rabbit anti-Parkin antibody M74 and mouse anti-polyubiquitine monoclonal antibody, and subsequent incubation with FITC-conjugated goat anti-rabbit IgG (Dako, Carpinteria, Calif.), biotinylated goat anti-mouse IgG (Sigma, St. Louis, Mo.) and avidin-rhodamine (Sigma). Signal was observed under a fluorescent confocal microscope MRC-1024 (Bio-Rad, Richmond, Calif.). The results of observation are shown in FIGS. 27 and 28.

Figure 27:
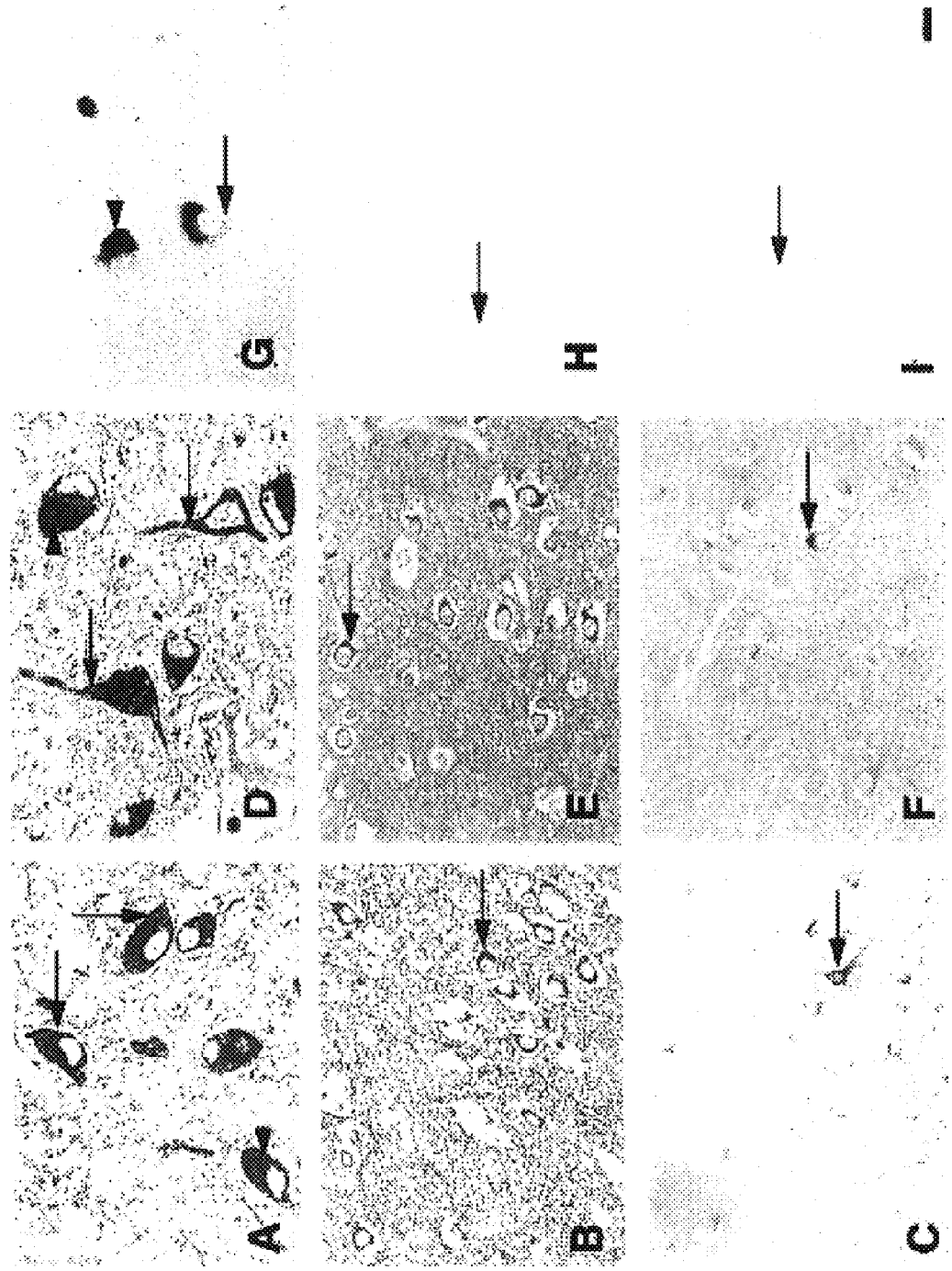
FIGS. 27A–27I are photomicrographs showing the result of immunohistochemical staining of the inventive gene that is expressed in brain sections.

FIG. 27 are photomicrographs of immunohistochemical staining with anti-Parkin antibody M-74 in the brain sections, wherein 27A to 27C show the result of a PD patient (case 2), 27D to 27F show that of a control subject (case 1), and 27G to 27I show that of a AR-JP patient (case 1). More specifically, the photomicrographs 27A, 27D, 27G show the melanin-containing neurons in the SN, 27B, 27E, 27H show the putamen, and 27C, 27F, 27I show the frontal lobe cortex. In the photomicrographs, the point of arrow indicates neuron, the root thereof indicates neuromelanin, and the unit length of bar thereof is 50 μm.

As can be seen from FIG. 27, melanin-containing neurons in the SN (including locus coeruleus) were most intensely stained in the PD patient and the control subject, but not in the AR-JP patient (FIGS. 27A, 27D, 27G). Further, in these melanin-containing neurons of the SN, cytoplasm and granular structure as well as neuronal processes were homogeneously stained. In contrast, no staining was seen in the nuclei. Some weak staining was observed in glial cells (FIGS. 27A to 27F). Neurons in the putamen and frontal lobe cortex from the PD patient and the control subject were weakly stained in the cytoplasm and perinuclear structures (FIGS. 27B, 27C, 27E, 27F).

Figure 28:
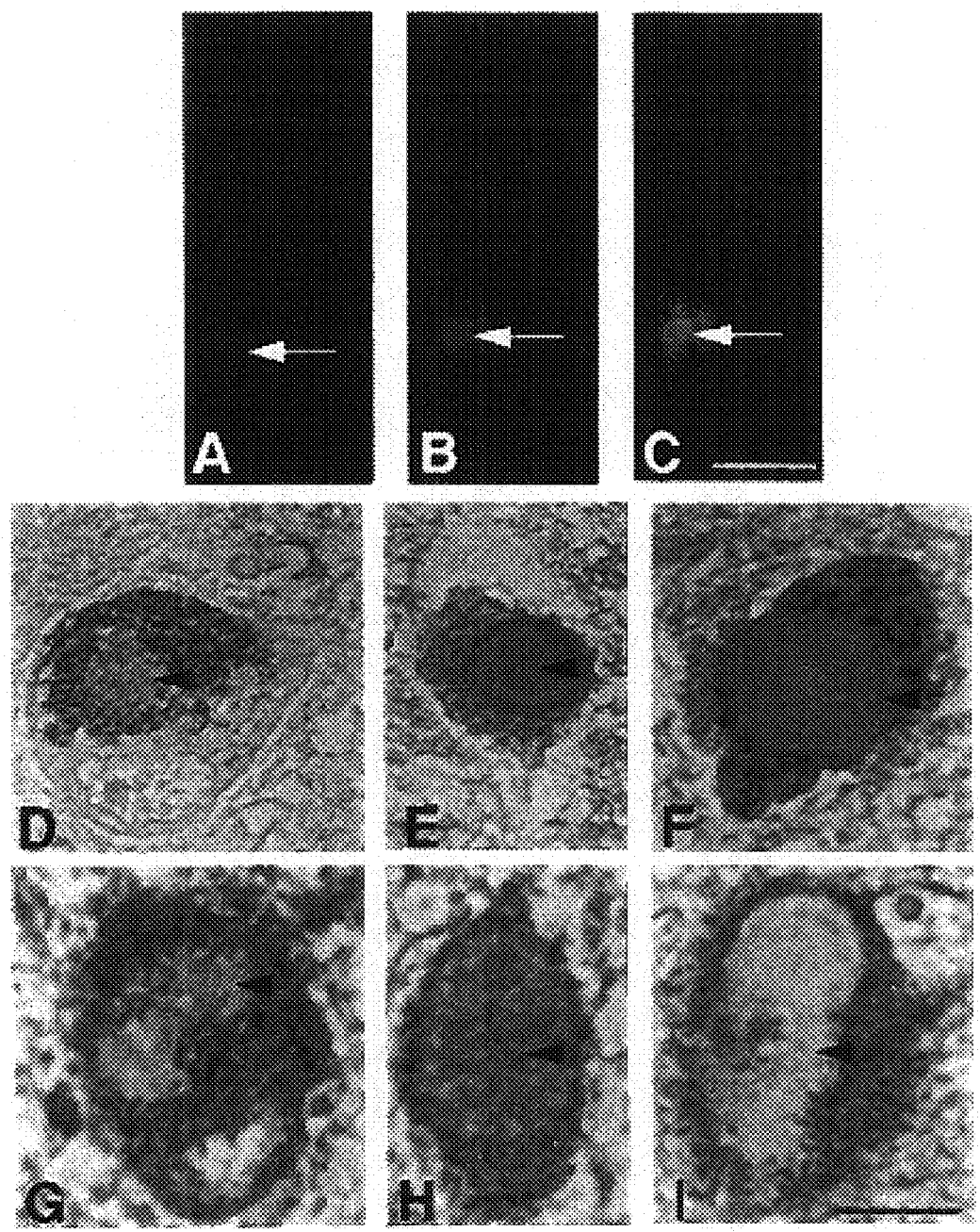
FIG. 28 is photomicrographs showing the result of immunostaining of the inventive gene that is expressed in brain sections, polyubiquitin, and α-synuclein.

FIG. 28 is photomicrographs of immunohistochemical staining with this inventive gene polyubiquitin, and α-synuclein in the brain sections, wherein 28A to 28C show the melanin-containing neuron in the SN of a PD patient (case 1) double-stained with anti-Parkin antibody M74 (green: A) and monoclonal anti-polyubiquitin antibody (red: B), 28D to 28F show midbrain cross-sections from the PD patient (case 1) stained with anti-α-synuclein antibody, and 28G to 28I show midbrain cross-sections from the PD patient (case 1) stained with anti-Parkin antibody M-74. In the photomicrographs of FIG. 28, the root of arrow indicates Lewy body, and the unit length of bar thereof is 50 μm.

As a result of double immunofluorescence, the anti-Parkin and anti-polyubiquitin antibodies in the Lewy body of melanin-containing neurons of the SN were stained (FIGS. 28A to 28C). As a result of immunostaining of cross-sections of midbrain, co-localization of this inventive gene and α-synuclein in some of Lewy bodies of the PD patient (FIGS. 28D, 28E, 28G, 28H) was observed. No such staining was observed in the brain tissues of the AR-JP patients (data not shown).

The above observation results verify that whereas the protein of this invention was observed in the brains of the sporadic PD patients and control subjects, this protein was not observed in the brains of the AR-JP patients. Also, the protein of this invention was found in Lewy body of the PD patients.

EXAMPLE 16

Immunoblotting of Inventive Gene in Juvenile Parkinson's Disease Patients

Followed by Example 15, in this Example, immunoblotting was carried out with respect to the inventive gene existing in the brains of AR-JP patients, PD patients and control subjects with use of antibodies against the protein of this invention.

Specifically, tissue blocks of frontal lobe cortex, substantia nigra and putamen of the subjects were homogenized with a Potter-Elvehjem homogenizer in an isotonic sucrose solution (10 mM Tris-HCl pH 7.4, 0.32M sucrose, 1 mM Zn-acetate, 15 μg/ml leupeptin, 5 μg/ml p-amidinophenylmethanesulfonyl fluoride hydrochloride (APMSF) and 50 ng/ml pepstatin). The homogenate was processed for 4 step-differential centrifugation to obtain the following fractions; Nuclear fraction (pellets after 600×g for 10 min.), mitochondrial fraction (pellets after 7,000×g for 10 min.), microsomal fraction (pellets after 100,000×g for 1 hr.) and cytosolic fraction (supernatant after 900,000×g for 1 hr.). The 900,000×g pellet was resuspended in TES buffer containing 0.25 M sucrose and layered over a step-gradient of sucrose (0.25M, 0.86M and 1.3M) and centrifuged in an SW28 rotor at 28,000 rpm for 1 hr. at 4° C. After lipid on the top layer was aspirated, the interface between 0.5M and 0.86M sucrose layers was collected as the Golgi fraction.

Proteins in these various fractions were separated on a 10% sodium dodecyl sulfate-polyacrylamide gel electrophoresis and transferred to PVDF membrane blots (Bio-Rad). The blots were soaked in Tris-buffered saline containing 0.05% Tween 20 and 5% bovine serum albumin (10 mM Tris-HCl, pH 7.6 and 150 mM NaCl) at 52° C. for 1 hr., probed with various antibodies such as anti-Parkin antibody M-74 in the blocking solution at 4° C. overnight, then washed with Tris-buffered saline containing 0.05% Tween 20. Anti-β-tubulin antibody (Amersham Life Science, Arlington, Ill.) was used as an internal control and anti-γ-adaptin antibody (Sigma) was used as a Golgi marker. Finally, blots were treated with peroxidase-conjugated goat anti-rabbit IgG (Dako) and anti-mouse IgG (Dako) at a room temperature for 1 hr. Then the reaction products were visualized using a chemi-luminescence reagent (Amersham, Buckinghamshire, UK).

Figure 29:
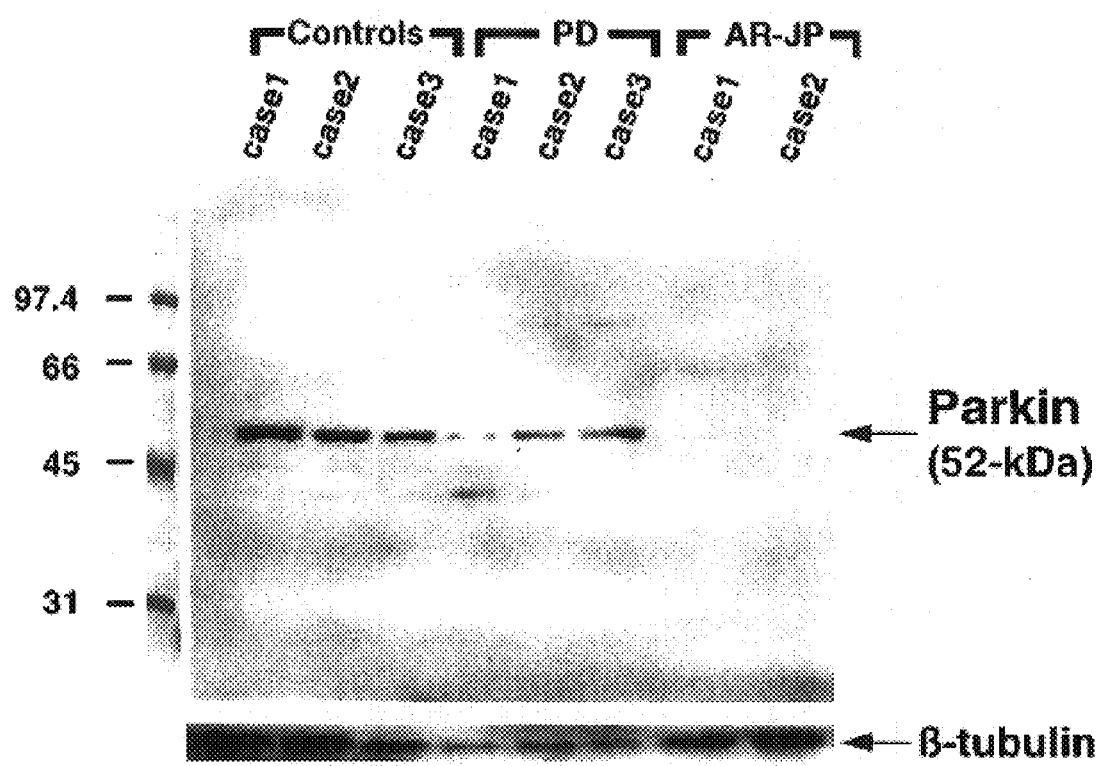
FIG. 29 is a diagram showing the result of immunoblotting the whole homogenates of the frontal lobe of control subjects, Parkinson's disease patients, and AR-JP patients.
Figure 30:
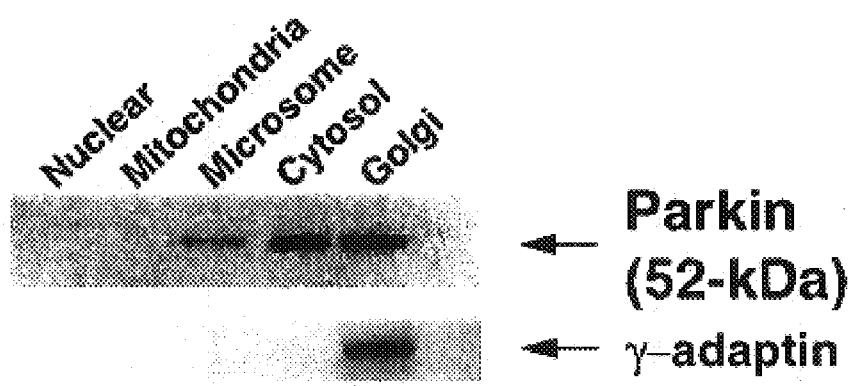
FIG. 30 is a diagram showing the result of immunoblotting the subcellular fractions of the frontal lobe tissue of a control subject.
Figure 31:
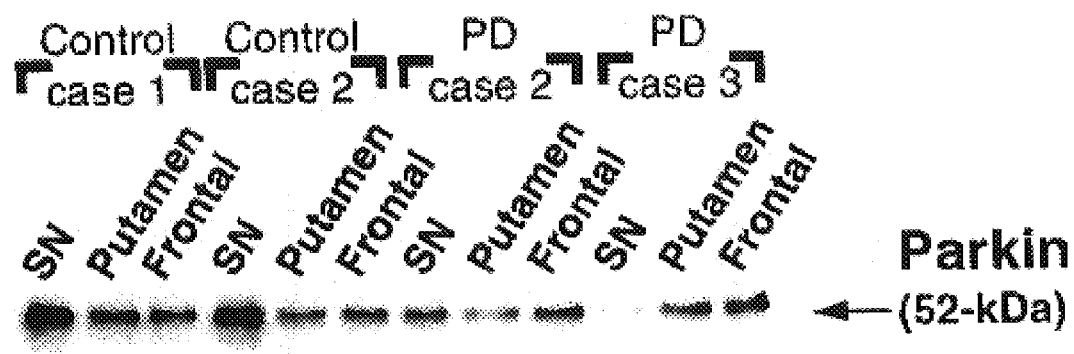
FIG. 31 is a diagram showing the result of immunoblotting the whole homogenates of the SN, putamen, and frontal lobe of control subjects, Parkinson's disease patients, and AR-JP patient.

The results of immunoblotting are shown in FIGS. 29 to 31. FIGS. 29 to 31 are microphotographs showing the results of immunoblotting the protein of this invention in various homogenates. FIG. 29 shows the result of whole homogenates of the frontal lobe of three control subjects (cases 1 to 3), three PD patients (cases 1 to 3) and two AR-JP patients (cases 1 and 2), wherein the left side gels are size markers, and β-tubulin is an internal marker. FIG. 30 shows the result of subcellular fractions of the frontal lobe tissue of the control subject (case 1) wherein nuclear, mitochondria, microsome, cytosol and Golgi are shown from left to right in the order, and γ-adaptin is a Golgi marker. FIG. 31 shows the result of whole homogenates of the SN, putamen and frontal lobe of the two control subjects (cases 1 and 2) and the two PD patients (cases 2 and 3).

As a result, the protein of this invention (in FIGS. denoted as "Parkin") of 52 kDa was detected in the whole homogenates of the frontal lobe cortex from the PD patients and the control subjects but not in those of the AR-JP patients (see FIG. 29). A second protein band of 41 kDa, possibly a processed form of Parkin protein, was found in the PD patients. Similar results were obtained using another antibody M-73 (data not shown).

After subcellular fractionation of the frontal lobe cortex homogenates of the control subject, majority of the inventive protein was found in the cytosol and Golgi fractions, and a minute amount of the inventive protein was found in the microsomal fraction (see FIG. 30).

Further, immunoblotting analysis of the homogenates of the SN, putamen and frontal lobe cortex from the control subjects and PD patients revealed that the inventive protein is more abundant in the SN as compared to the other parts of the brain (see FIG. 31). The inventive protein in the SN Of the Parkinson's disease patients was obviously reduced in agreement with the loss of nigral neurons in the PD patients.

The above results verified that the protein of this invention was not detected in any brain section of the AR-JP patients and that this protein exists in the melanin-containing neurons in the SN.

EXAMPLE 17

Polymorphism of the Parkin Gene in Sporadic Parkinson's Disease (PD) Patients and Control Subjects In this Example, polymorphism frequency in PD was investigated. Specifically, hereditary polymorphism was analyzed according to the following procedure with respect to the subjects consisting of 160 PD patients and 160 control subjects without neurodegenerative disorders. In this Example, patients with the age of onset below 40 years old were excluded. The average age of onset was 55.4±10.7. None of the PD patients had family history of PD, nor diurnal fluctuations of symptoms. The age of the control subjects was from 40 to 98 years old.

Human genomic DNA was extracted from the peripheral leukocytes of the subjects. Samples were either used immediately or stored at −20° C. until analyzed. Exons 4 and 10 of the Parkin gene were amplified by PCR using two primer pairs (exon 4: forward primer, 5'-acaagcttttaaagagtttcttgt-3' (SEQ ID NO:39), reverse primer, 5'-aggcaatgtgttagtacaca-3' (SEQ ID NO:40), exon 10: forward primer, 5'-attgccaaatgcaacctaatgtc-3' (SEQ ID NO:53), reverse primer, 5'-ttggaggaatgagtagggcatt-3' (SEQ ID NO:54)).

Polymorphism that replaces Ser at amino acid position 167 to Asn (S167N) (replacement of G to A) was found in exon 4. Polymorphisms that replace Arg at amino acid position 366 to Trp (R366W) (replacement of C to T) and Val at amino position 380 to Leu (V380L) (replacement of G to C) respectively were found in exon 10. Alleles of the polymorphisms S167N, R366W, and V380L were respectively identified by digestion with AlwNI, NciI, BsP1286I. Whereas both the S167N and R366W wild alleles created restriction sites for AlwNI and NciI, respectively, the V380L mutant allele created a restriction site for Bsp 1286I, thus identifying wild allele and mutant allele.

Figure 32:
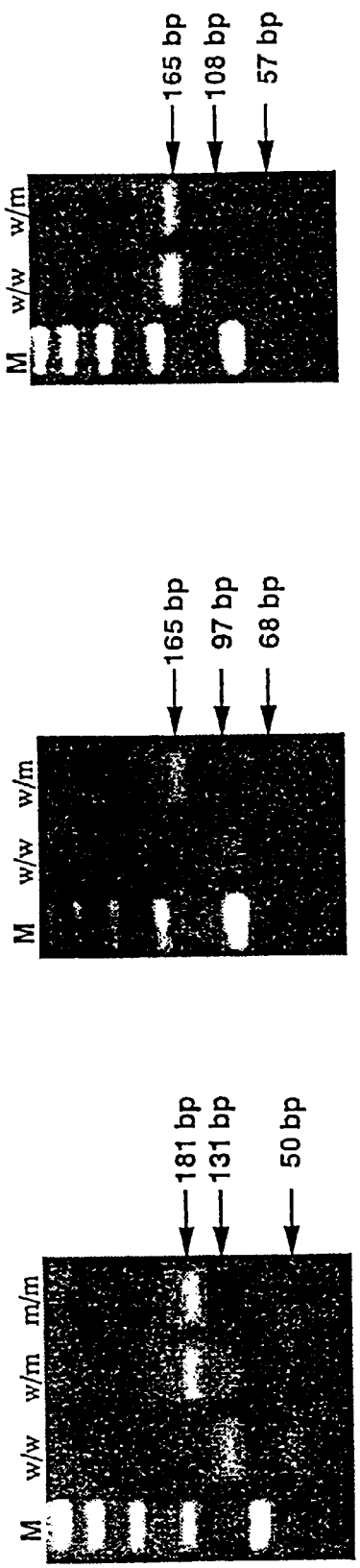
FIGS. 32A–32C are diagrams showing the result of gel electrophoresis of PCR products from exon 4 and exon 10.

More specifically, the PCR products were electrophoresed on 3% agarose gel and then visualized with ethidium bromide. As a result, as shown in FIG. 32, a band spanning 50 bp/131 bp was found by digestion with AlwNI [see FIG. 32 A)], a band spanning 68 bp/97 bp was found by digestion with NciI [see FIG. 32 B)], and a band spanning 57 bp/108 bp was found by digestion with Bsp1286I [see FIG. 32 C)].

More specifically, the PCR conditions for exon 4 were as follows. The initial denaturation was performed at 94° C. for 10 min., followed by 40 cycles of denaturation at 94° C. for 30 sec., annealing at 53° C. for 1 min, and extension at 72° C. for 1 min., with a final extension at 72° C. for 10 min. The PCR conditions for exon 10 were as follows. The initial denaturation was performed at 94° C. for 10 min., followed by 40 cycles of denaturation at 94° C. for 30 sec., annealing at 55° C. for 30 sec., and extension at 72° C. for 45 sec., with a final extension at 72° C. for 10 min.

Subsequently, frequencies of wild-type homozygotes (w/w), wild/mutant heterozygotes (w/m), and mutant homozygotes (m/m) were examined.

Tables 4 and 5 show the wild allele and genotype frequencies of the polymorphism S167N. Expected values in Table 5 were calculated according to the Hardy-Weinberg equilibrium.

TABLE 4

|  | Control (%) | PD (%) | Total (%) |
|---|---|---|---|
| No. of Subjects | 160 | 160 | 320 |
| No. of Chromosomes | 320 | 320 | 640 |
| Allele G | 180 (56.3%) | 181 (56.6%) | 361 (56.4%) |
| Allele A | 140 (43.7%) | 139 (43.4%) | 279 (43.6%) |
|  | $\chi^2 = 0.006$, d.f. = 0.936[a] | | |

Remarks
[a]: No significant difference in allele frequencies between the PD patients and the control.
Note:
Expected values were calculated according to the Hardy-Weinberg equilibrium.

TABLE 5

| | Control (%) | | PD (%) | | |
|---|---|---|---|---|---|
| | Observed | Expected | Observed | Expected | Total (%) |
| GG | 58 (36.3%) | 51 | 59 (36.9%) | 51 | 117 (36.6%) |
| GA | 64 (40.0%) | 79 | 63 (39.4%) | 79 | 127 (39.7%) |
| AA | 38 (23.7%) | 30 | 38 (23.7%) | 30 | 76 (23.7%) |

$\chi^2 = 2.97$, d.f. = 2, p = 0.227[b]
$\chi^2 = 3.33$, d.f. = 2, p = 0.189[c]
$\chi^2 = 0.016$, d.f. = 2, p = 0.992[d]

Remarks:
[b]: The expected frequencies versus observed frequencies of the genotype in the control.
[c]: The expected versus observed frequencies of the genotype in the PD patients.
[d]: No significant difference in the genotype distribution between the PD patients and the controls.

The above results show that there is no significant difference between the PD patients and the control subjects with respect to allele and genotype frequency. Further, the frequencies of both −167Ser homozygote and −167Ser/Asn heterozygotes did not differ significantly between the two groups.

Further, Table 5 shows that the observed frequencies of three genotypes did not significantly differ between the expected frequencies of the control subjects and those of the patients. Computer analysis verified that this replacement did not cause changes in the secondary structure of the gene products.

Table 6 shows the allele and genotype frequencies of the polymorphism V380L.

TABLE 6

| | Control (%) | PD (%) | Total (%) |
|---|---|---|---|
| No. of Subjects | 160 | 160 | 320 |
| No. of Chromosomes | 320 | 320 | 640 |
| Allele G | 309 (96.6%) | 314 (98.1%) | 623 (97.3%) |
| Allele C | 11 (3.4%) | 6 (1.9%) | 17 (2.7%) |

$\chi^2 = 1.51$, d.f. = 1, p = 0.219[a]

Remarks
[a]: No significant difference in allele frequencies between the PD patients and the controls.

As shown in Table 6, there was no significant difference in allele frequencies of the polymorphism V380L between the PD patients and the controls. Further, it was verified that the observed frequencies of the polymorphism V380L conformed with the expected frequencies and that the secondary structure of the gene product did not change due to this polymorphic mutation.

Next, Table 7 shows the allele and genotype frequencies of the polymorphism R366W.

TABLE 7

| | Control (%) | PD (%) | Total (%) |
|---|---|---|---|
| No. of Subjects | 160 | 160 | 320 |
| No. of Chromosomes | 320 | 320 | 640 |
| Allele C | 306 (95.6%) | 316 (98.8%) | 622 (97.2%) |
| Allele T | 14 (4.4%) | 4 (1.2%) | 18 (2.8%) |

$\chi^2 = 5.72$, d.f. = 1, p = 0.017[a]

Remarks
[a]: No significant difference in allele frequencies between the PD patients and the control subjects.
(Fisher's exact probability test, p = 0.014 < 0.02, Odds ratio = 3.60, 95% CI: 0.45–6.50).

Regarding the polymorphism R366W, the expected frequencies of the three genotypes were exactly same between the PD patients and the control subjects. However, the allele frequency of R366W differed significantly between the PD patients and the control subjects. Specifically, while the allele frequency in the PD patients was 1.2%, that in the control subjects was 4.4%. This result shows that the allele frequency in the PD patients significantly lowered compared to that in the control subjects. The odd ratio (possession ratio of allele of control subjects to PD patients) was 3.60.

Figure 33:
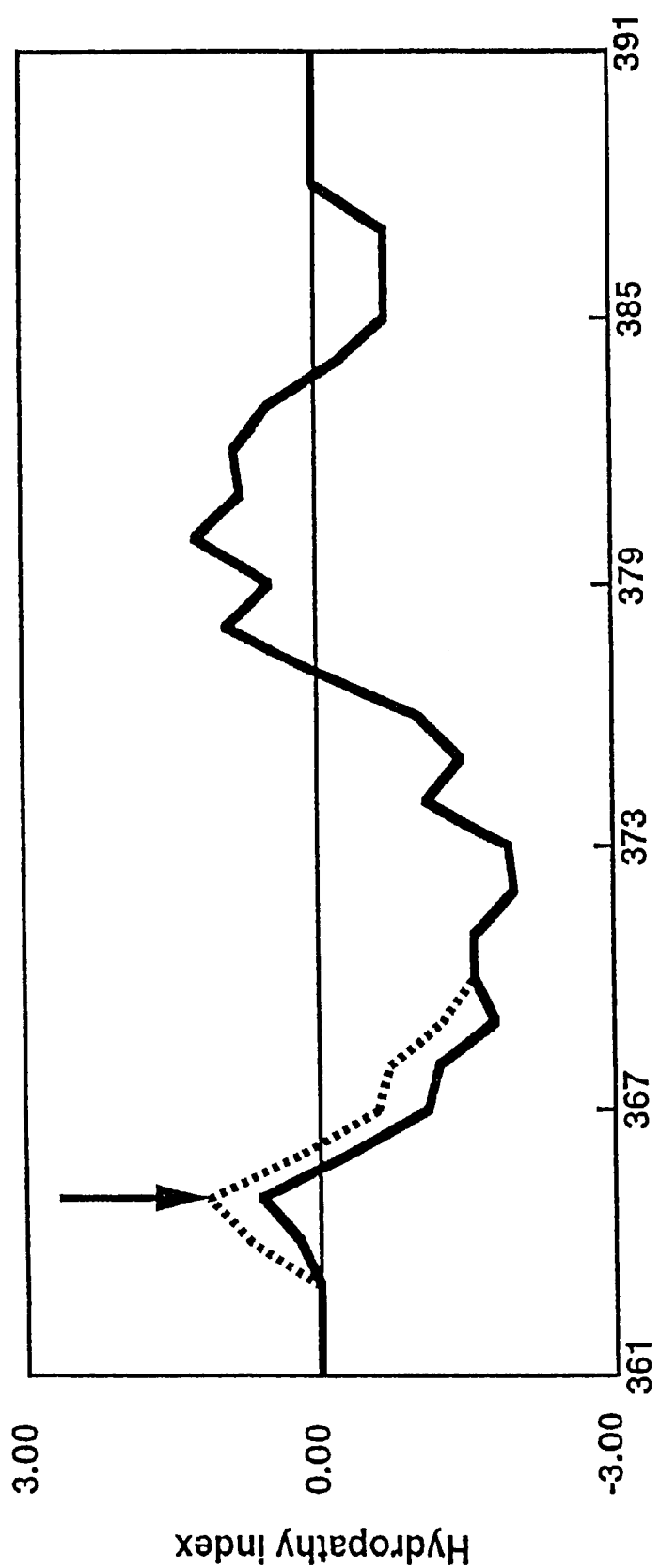
FIG. 33 is a graph obtained by hydropathy plot of the amino acid sequence of this inventive protein.

FIG. 33 is a graph representing hydropathy index of amino acid sequence in the polymorphism R366W. (+) and (−) regions in FIG. 33 represents hydrophobic and hydrophilic regions, respectively. The point shown by the arrow in FIG. 33 indicates the change from hydrophilicity to hydrophobicity that is caused by replacement of −366 Arg with Trp.

Figure 34:
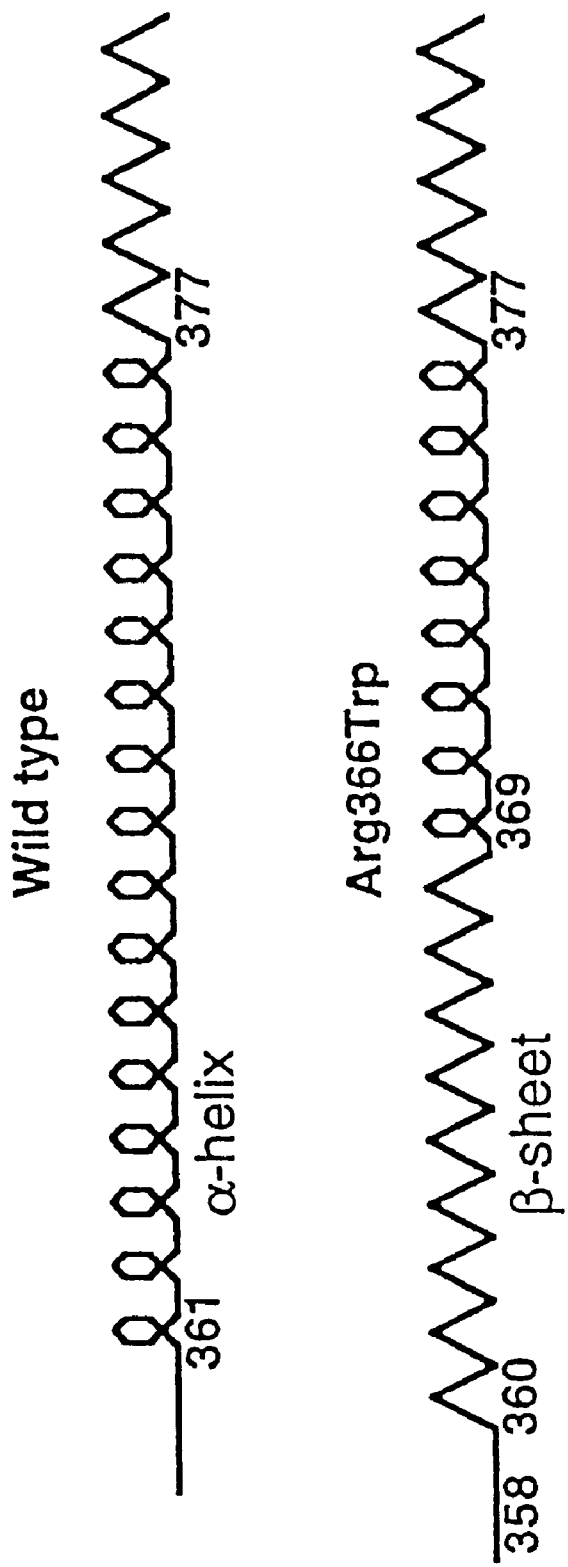
FIG. 34 is a diagram showing that replacement of 366 Arg to Trp changes α helix portion to β-sheet structure.

FIG. 34 is a diagram showing a secondary structural change in the polymorphism R366W. This diagram shows that replacement of −366 Arg with Trp changes the α-helix (at position 361 to 376) to the β-sheet structure (at position 360–360).

This Example shows that although S167N and V380L among the three polymorphisms did not crucially influence the gene product of the PD patients, the allele frequency of polymorphism R366W was extremely low in the PD patients, and the odd ratio was calculated as 3.60. This result suggests that the allele constitute a protective factor against PD which inhibits onset of PD.

EXPLOITATION IN INDUSTRY

The invention of this application has the above-mentioned arrangements described in terms of various aspects. The aforementioned various examples and descriptions not only identified the gene responsible for Parkinson's disease but also clarified that partial deletion or mutation etc., of the gene of this invention induces Parkinson's disease. Accordingly, onset of Parkinson's disease is easily judged by detecting the presence or absence of abnormality of the inventive gene, which is very useful in diagnosing Parkinson's disease at an initial or early stage thereof.

So-called "gene therapy" for treating Parkinson's disease patients with use of the inventive gene is also possible. Further, recombinant protein obtainable from the inventive gene is useful as a drug for preventing and/or treating Parkinson's disease. Antibody (monoclonal antibody and polyclonal antibody) against such a recombinant protein can be used for diagnosis etc., of Parkinson's disease. Utilizing such a recombinant protein enables one to synthesize a pharmaceutically effective agent that is significantly useful in preventing, treating, and diagnosing Parkinson's disease etc. Thus the present invention possesses significant usability in industry because the present invention can contribute to development of various gene therapies and pharmaceutical compositions effective in various diseases focusing on parkinson's disease and parkinson-related diseases.

What is claimed is:

1. An isolated polynucleotide comprising a nucleotide sequence encoding amino acids 4–57 of SEQ ID NO:2.

2. The isolated polynucleotide of claim 1 comprising a nucleotide sequence encoding amino acids 1–72 of SEQ ID NO:2.

3. The isolated polynucleotide of claim 2 comprising a nucleotide sequence encoding amino acids 1–437 of SEQ ID NO:4.

4. The isolated polynucleotide of claim 4 comprising a nucleotide sequence encoding amino acids 1–465 of SEQ ID NO:2.

5. An isolated polynucleotide comprising a nucleotide sequence complementary to the nucleotide sequence of claim 1.

6. An isolated polynucleotide comprising a nucleotide sequence complementary to the nucleotide sequence of claim 2.

7. An isolated polynucleotide comprising a nucleotide sequence complementary to the nucleotide sequence of claim 3.

8. An isolated polynucleotide comprising a nucleotide sequence complementary to the nucleotide sequence of claim 4.

9. A recombinant vector comprising the polynucleotide of claim 1.

10. A recombinant vector comprising the polynucleotide of claim 2.

11. A recombinant vector comprising the polynucleotide of claim 3.

12. A recombinant vector comprising the polynucleotide of claim 4.

* * * * *

UNITED STATES PATENT AND TRADEMARK OFFICE
CERTIFICATE OF CORRECTION

PATENT NO. : 6,716,621 B1
DATED : April 6, 2004
INVENTOR(S) : Shimizu et al.

It is certified that error appears in the above-identified patent and that said Letters Patent is hereby corrected as shown below:

<u>Column 67,</u>
Line 33, please delete "of claim 4 comprising" and insert therein -- of claim 2 comprising --.

Signed and Sealed this

Third Day of August, 2004

JON W. DUDAS
*Acting Director of the United States Patent and Trademark Office*

SEQUENCE LISTING

<160> NUMBER OF SEQ ID NOS: 70

<210> SEQ ID NO 1
<211> LENGTH: 2960
<212> TYPE: DNA
<213> ORGANISM: Homo sapiens
<220> FEATURE:
<221> NAME/KEY: CDS
<222> LOCATION: (102)..(1496)
<223> OTHER INFORMATION:
<220> FEATURE:
<221> NAME/KEY: misc_feature
<222> LOCATION: (102)..(108)
<223> OTHER INFORMATION: Exon 1
<220> FEATURE:
<221> NAME/KEY: misc_feature
<222> LOCATION: (109)..(272)
<223> OTHER INFORMATION: Exon 2
<220> FEATURE:
<221> NAME/KEY: misc_feature
<222> LOCATION: (273)..(513)
<223> OTHER INFORMATION: Exon 3
<220> FEATURE:
<221> NAME/KEY: misc_feature
<222> LOCATION: (514)..(635)
<223> OTHER INFORMATION: Exon 4
<220> FEATURE:
<221> NAME/KEY: misc_feature
<222> LOCATION: (636)..(719)
<223> OTHER INFORMATION: Exon 5
<220> FEATURE:
<221> NAME/KEY: misc_feature
<222> LOCATION: (720)..(835)
<223> OTHER INFORMATION: Exon 6
<220> FEATURE:
<221> NAME/KEY: misc_feature
<222> LOCATION: (836)..(972)
<223> OTHER INFORMATION: Exon 7
<220> FEATURE:
<221> NAME/KEY: misc_feature
<222> LOCATION: (973)..(1034)
<223> OTHER INFORMATION: Exon 8
<220> FEATURE:
<221> NAME/KEY: misc_feature
<222> LOCATION: (1035)..(1184)
<223> OTHER INFORMATION: Exon 9
<220> FEATURE:
<221> NAME/KEY: misc_feature
<222> LOCATION: (1185)..(1268)
<223> OTHER INFORMATION: Exon 10
<220> FEATURE:
<221> NAME/KEY: misc_feature
<222> LOCATION: (1269)..(1386)
<223> OTHER INFORMATION: Exon 11
<220> FEATURE:
<221> NAME/KEY: misc_feature
<222> LOCATION: (1387)..(2960)
<223> OTHER INFORMATION: Exon 12

<400> SEQUENCE: 1

```
tccgggagga ttacccagga gaccgctggt gggaggcgcg gctggcgccg ctgcgcgcat        60
gggcctgttc ctggcccgca gccgccacct acccagtgac c atg ata gtg ttt gtc      116
                                              Met Ile Val Phe Val
                                                1               5 agg ttc aac tcc agc cat ggt ttc cca gtg gag gtc gat tct gac acc        164
Arg Phe Asn Ser Ser His Gly Phe Pro Val Glu Val Asp Ser Asp Thr
             10                  15                  20 agc atc ttc cag ctc aag gag gtg gtt gct aag cga cag ggg gtt ccg        212
Ser Ile Phe Gln Leu Lys Glu Val Val Ala Lys Arg Gln Gly Val Pro
         25                  30                  35 gct gac cag ttg cgt gtg att ttc gca ggg aag gag ctg agg aat gac        260
```

| | | | | | | | | | | | | |
|---|---|---|---|---|---|---|---|---|---|---|---|---|
| Ala | Asp | Gln | Leu | Arg | Val | Ile | Phe | Ala | Gly | Lys | Glu | Leu | Arg | Asn | Asp |
| | | | 40 | | | | | 45 | | | | | 50 | | |

```
tgg act gtg cag aat tgt gac ctg gat cag cag agc att gtt cac att        308
Trp Thr Val Gln Asn Cys Asp Leu Asp Gln Gln Ser Ile Val His Ile
     55                  60                  65 gtg cag aga ccg tgg aga aaa ggt caa gaa atg aat gca act gga ggc        356
Val Gln Arg Pro Trp Arg Lys Gly Gln Glu Met Asn Ala Thr Gly Gly
70              75                  80                  85 gac gac ccc aga aac gcg gcg gga ggc tgt gag cgg gag ccc cag agc        404
Asp Asp Pro Arg Asn Ala Ala Gly Gly Cys Glu Arg Glu Pro Gln Ser
                90                  95                  100 ttg act cgg gtg gac ctc agc agc tca gtc ctc cca gga gac tct gtg        452
Leu Thr Arg Val Asp Leu Ser Ser Ser Val Leu Pro Gly Asp Ser Val
             105                 110                 115 ggg ctg gct gtc att ctg cac act gac agc agg aag gac tca cca cca        500
Gly Leu Ala Val Ile Leu His Thr Asp Ser Arg Lys Asp Ser Pro Pro
         120                 125                 130 gct gga agt cca gca ggt aga tca atc tac aac agc ttt tat gtg tat        548
Ala Gly Ser Pro Ala Gly Arg Ser Ile Tyr Asn Ser Phe Tyr Val Tyr
     135                 140                 145 tgc aaa ggc ccc tgt caa aga gtg cag ccg gga aaa ctc agg gta cag        596
Cys Lys Gly Pro Cys Gln Arg Val Gln Pro Gly Lys Leu Arg Val Gln
150                 155                 160                 165 tgc agc acc tgc agg cag gca acg ctc acc ttg acc cag ggt cca tct        644
Cys Ser Thr Cys Arg Gln Ala Thr Leu Thr Leu Thr Gln Gly Pro Ser
                170                 175                 180 tgc tgg gat gat gtt tta att cca aac cgg atg agt ggt gaa tgc caa        692
Cys Trp Asp Asp Val Leu Ile Pro Asn Arg Met Ser Gly Glu Cys Gln
             185                 190                 195 tcc cca cac tgc cct ggg act agt gca gaa ttt ttc ttt aaa tgt gga        740
Ser Pro His Cys Pro Gly Thr Ser Ala Glu Phe Phe Phe Lys Cys Gly
         200                 205                 210 gca cac ccc acc tct gac aag gaa aca cca gta gct ttg cac ctg atc        788
Ala His Pro Thr Ser Asp Lys Glu Thr Pro Val Ala Leu His Leu Ile
     215                 220                 225 gca aca aat agt cgg aac atc act tgc att acg tgc aca gac gtc agg        836
Ala Thr Asn Ser Arg Asn Ile Thr Cys Ile Thr Cys Thr Asp Val Arg
230                 235                 240                 245 agc ccc gtc ctg gtt ttc cag tgc aac tcc cgc cac gtg att tgc tta        884
Ser Pro Val Leu Val Phe Gln Cys Asn Ser Arg His Val Ile Cys Leu
                250                 255                 260 gac tgt ttc cac tta tac tgt gtg aca aga ctc aat gat cgg cag ttt        932
Asp Cys Phe His Leu Tyr Cys Val Thr Arg Leu Asn Asp Arg Gln Phe
             265                 270                 275 gtt cac gac cct caa ctt ggc tac tcc ctg cct tgt gtg gct ggc tgt        980
Val His Asp Pro Gln Leu Gly Tyr Ser Leu Pro Cys Val Ala Gly Cys
         280                 285                 290 ccc aac tcc ttg att aaa gag ctc cat cac ttc agg att ctg gga gaa       1028
Pro Asn Ser Leu Ile Lys Glu Leu His His Phe Arg Ile Leu Gly Glu
     295                 300                 305 gag cag tac aac cgg tac cag cag tat ggt gca gag gag tgt gtc ctg       1076
Glu Gln Tyr Asn Arg Tyr Gln Gln Tyr Gly Ala Glu Glu Cys Val Leu
310                 315                 320                 325 cag atg ggg ggc gtg tta tgc ccc cgc cct ggc tgt gga gcg ggg ctg       1124
Gln Met Gly Gly Val Leu Cys Pro Arg Pro Gly Cys Gly Ala Gly Leu
                330                 335                 340 ctg ccg gag cct gac cag agg aaa gtc acc tgc gaa ggg ggc aat ggc       1172
Leu Pro Glu Pro Asp Gln Arg Lys Val Thr Cys Glu Gly Gly Asn Gly
             345                 350                 355
```

```
ctg ggc tgt ggg ttt gcc ttc tgc cgg gaa tgt aaa gaa gcg tac cat      1220
Leu Gly Cys Gly Phe Ala Phe Cys Arg Glu Cys Lys Glu Ala Tyr His
        360                 365                 370 gaa ggg gag tgc agt gcc gta ttt gaa gcc tca gga aca act act cag      1268
Glu Gly Glu Cys Ser Ala Val Phe Glu Ala Ser Gly Thr Thr Thr Gln
    375                 380                 385 gcc tac aga gtc gat gaa aga gcc gcc gag cag gct cgt tgg gaa gca      1316
Ala Tyr Arg Val Asp Glu Arg Ala Ala Glu Gln Ala Arg Trp Glu Ala
390                 395                 400                 405 gcc tcc aaa gaa acc atc aag aaa acc acc aag ccc tgt ccc cgc tgc      1364
Ala Ser Lys Glu Thr Ile Lys Lys Thr Thr Lys Pro Cys Pro Arg Cys
                410                 415                 420 cat gta cca gtg gaa aaa aat gga ggc tgc atg cac atg aag tgt ccg      1412
His Val Pro Val Glu Lys Asn Gly Gly Cys Met His Met Lys Cys Pro
            425                 430                 435 cag ccc cag tgc agg ctc gag tgg tgc tgg aac tgt ggc tgc gag tgg      1460
Gln Pro Gln Cys Arg Leu Glu Trp Cys Trp Asn Cys Gly Cys Glu Trp
        440                 445                 450 aac cgc gtc tgc atg ggg gac cac tgg ttc gac gtg tagccagggc           1506
Asn Arg Val Cys Met Gly Asp His Trp Phe Asp Val
    455                 460                 465 ggccgggcgc cccatcgcca catcctgggg gagcataccc agtgtctacc ttcattttct    1566
aattctcttt tcaaacacac acacacacgc gcgcgcgcgc acacacactc ttcaagtttt    1626
tttcaaagtc caactacagc caaattgcag aagaaactcc tggatccctt tcactatgtc    1686
catgaaaaac agcagagtaa aattacgaaa gaagctcctg aatccctttc agtttgtcca    1746
cacaagacag cagagccatc tgcgacacca ccaacaggcg ttctcagcct ccggatgaca    1806
caaataccag agcacagatt caagtgcaat ccatgtatct gtatgggtca ttctcacctg    1866
aattcgagac aggcagaatc agtagctgga gagagagttc tcacatttaa tatcctgcct    1926
tttaccttca gtaaacacca tgaagatgcc attgacaagg tgtttctctg taaaatgaac    1986
tgcagtgggt tctccaaact agattcatgg ctttaacagt aatgttctta tttaaatttt    2046
cagaaagcat ctattcccaa agaaccccag gcaatagtca aaaacatttg tttatcctta    2106
agaattccat ctatataaat cgcattaatc gaaataccaa ctatgtgtaa atcaacttgt    2166
cacaaagtga gaaattatga agttaatttt gaatgttgaa tgtttgaatt acagggaaga    2226
aatcaagtta atgtactttc attccctttc atgatttgca actttagaaa gaaattgttt    2286
ttctgaaagt atcaccaaaa aatctatagt ttgattctga gtattcattt tgcaacttgg    2346
agattttgct aatacatttg gctccactgt aaatttaata gataaagtgc ctataaagga    2406
aacacgttta gaaatgattt caaaatgata ttcaatctta acaaaagtga acattattaa    2466
atcagaatct ttaaagagga gcctttccag aactaccaaa atgaagacac gcccgactct    2526
ctccatcaga agggtttata cccctttggc acaccctctc tgtccaatct gcaagtccca    2586
gggagctctg cataccaggg gttccccagg agagaccttc tcttaggaca gtaaactcac    2646
tagaatattc cttatgttga catggattgg atttcagttc aatcaaactt tcagcttttt    2706
tttcagccat tcacaacaca atcaaaagat taacaacact gcatgcggca aaccgcatgc    2766
tcttacccac actacgcaga agagaaagta caacccactat cttttgttct acctgtattg    2826
tctgacttct caggaagatc gtgaacataa ctgagggcat gagtctcact agcacatgga    2886
ggcccttttg gatttagaga ctgtaaatta ttaaatcggc aacagggctt ctctttttag    2946
atgtagcact gaaa                                                      2960
```

```
<210> SEQ ID NO 2
<211> LENGTH: 465
<212> TYPE: PRT
<213> ORGANISM: Homo sapiens

<400> SEQUENCE: 2

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Pro Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Gly Cys Ser Ala Val Phe Glu Ala Ser
370                 375                 380
```

```
Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
            405                 410                 415

Pro Cys Pro Arg Cys His Val Pro Val Glu Lys Asn Gly Gly Cys Met
                420                 425                 430

His Met Lys Cys Pro Gln Pro Gln Cys Arg Leu Glu Trp Cys Trp Asn
        435                 440                 445

Cys Gly Cys Glu Trp Asn Arg Val Cys Met Gly Asp His Trp Phe Asp
    450                 455                 460

Val
465

<210> SEQ ID NO 3
<211> LENGTH: 2876
<212> TYPE: DNA
<213> ORGANISM: Homo sapiens
<220> FEATURE:
<221> NAME/KEY: CDS
<222> LOCATION: (102)..(1412)
<223> OTHER INFORMATION:
<220> FEATURE:
<221> NAME/KEY: misc_feature
<222> LOCATION: (102)..(108)
<223> OTHER INFORMATION: Exon 1
<220> FEATURE:
<221> NAME/KEY: misc_feature
<222> LOCATION: (109)..(272)
<223> OTHER INFORMATION: Exon 2
<220> FEATURE:
<221> NAME/KEY: misc_feature
<222> LOCATION: (273)..(513)
<223> OTHER INFORMATION: Exon 3
<220> FEATURE:
<221> NAME/KEY: misc_feature
<222> LOCATION: (514)..(635)
<223> OTHER INFORMATION: Exon 4
<220> FEATURE:
<221> NAME/KEY: misc_feature
<222> LOCATION: (636)..(751)
<223> OTHER INFORMATION: Exon 6
<220> FEATURE:
<221> NAME/KEY: misc_feature
<222> LOCATION: (752)..(888)
<223> OTHER INFORMATION: Exon 7
<220> FEATURE:
<221> NAME/KEY: misc_feature
<222> LOCATION: (889)..(950)
<223> OTHER INFORMATION: Exon 8
<220> FEATURE:
<221> NAME/KEY: misc_feature
<222> LOCATION: (951)..(1100)
<223> OTHER INFORMATION: Exon 9
<220> FEATURE:
<221> NAME/KEY: misc_feature
<222> LOCATION: (1101)..(1184)
<223> OTHER INFORMATION: Exon 10
<220> FEATURE:
<221> NAME/KEY: misc_feature
<222> LOCATION: (1185)..(1302)
<223> OTHER INFORMATION: Exon 11
<220> FEATURE:
<221> NAME/KEY: misc_feature
<222> LOCATION: (1303)..(2876)
<223> OTHER INFORMATION: Exon 11

<400> SEQUENCE: 3
tccgggagga ttacccagga gaccgctggt gggaggcgcg gctggcgccg ctgcgcgcat      60
gggcctgttc ctggcccgca gccgccacct acccagtgac c atg ata gtg ttt gtc    116
                                            Met Ile Val Phe Val
                                              1               5
```

```
agg ttc aac tcc agc cat ggt ttc cca gtg gag gtc gat tct gac acc     164
Arg Phe Asn Ser Ser His Gly Phe Pro Val Glu Val Asp Ser Asp Thr
            10                  15                  20 agc atc ttc cag ctc aag gag gtg gtt gct aag cga cag ggg gtt ccg     212
Ser Ile Phe Gln Leu Lys Glu Val Val Ala Lys Arg Gln Gly Val Pro
        25                  30                  35 gct gac cag ttg cgt gtg att ttc gca ggg aag gag ctg agg aat gac     260
Ala Asp Gln Leu Arg Val Ile Phe Ala Gly Lys Glu Leu Arg Asn Asp
            40                  45                  50 tgg act gtg cag aat tgt gac ctg gat cag cag agc att gtt cac att     308
Trp Thr Val Gln Asn Cys Asp Leu Asp Gln Gln Ser Ile Val His Ile
        55                  60                  65 gtg cag aga ccg tgg aga aaa ggt caa gaa atg aat gca act gga ggc     356
Val Gln Arg Pro Trp Arg Lys Gly Gln Glu Met Asn Ala Thr Gly Gly
70              75                  80                  85 gac gac ccc aga aac gcg gcg gga ggc tgt gag cgg gag ccc cag agc     404
Asp Asp Pro Arg Asn Ala Ala Gly Gly Cys Glu Arg Glu Pro Gln Ser
            90                  95                  100 ttg act cgg gtg gac ctc agc agc tca gtc ctc cca gga gac tct gtg     452
Leu Thr Arg Val Asp Leu Ser Ser Ser Val Leu Pro Gly Asp Ser Val
        105                 110                 115 ggg ctg gct gtc att ctg cac act gac agc agg aag gac tca cca cca     500
Gly Leu Ala Val Ile Leu His Thr Asp Ser Arg Lys Asp Ser Pro Pro
            120                 125                 130 gct gga agt cca gca ggt aga tca atc tac aac agc ttt tat gtg tat     548
Ala Gly Ser Pro Ala Gly Arg Ser Ile Tyr Asn Ser Phe Tyr Val Tyr
        135                 140                 145 tgc aaa ggc ccc tgt caa aga gtg cag ccg gga aaa ctc agg gta cag     596
Cys Lys Gly Pro Cys Gln Arg Val Gln Pro Gly Lys Leu Arg Val Gln
150             155                 160                 165 tgc agc acc tgc agg cag gca acg ctc acc ttg acc cag gaa ttt ttc     644
Cys Ser Thr Cys Arg Gln Ala Thr Leu Thr Leu Thr Gln Glu Phe Phe
            170                 175                 180 ttt aaa tgt gga gca cac ccc acc tct gac aag gaa aca cca gta gct     692
Phe Lys Cys Gly Ala His Pro Thr Ser Asp Lys Glu Thr Pro Val Ala
        185                 190                 195 ttg cac ctg atc gca aca aat agt cgg aac atc act tgc att acg tgc     740
Leu His Leu Ile Ala Thr Asn Ser Arg Asn Ile Thr Cys Ile Thr Cys
        200                 205                 210 aca gac gtc agg agc ccc gtc ctg gtt ttc cag tgc aac tcc cgc cac     788
Thr Asp Val Arg Ser Pro Val Leu Val Phe Gln Cys Asn Ser Arg His
        215                 220                 225 gtg att tgc tta gac tgt ttc cac tta tac tgt gtg aca aga ctc aat     836
Val Ile Cys Leu Asp Cys Phe His Leu Tyr Cys Val Thr Arg Leu Asn
230             235                 240                 245 gat cgg cag ttt gtt cac gac cct caa ctt ggc tac tcc ctg cct tgt     884
Asp Arg Gln Phe Val His Asp Pro Gln Leu Gly Tyr Ser Leu Pro Cys
            250                 255                 260 gtg gct ggc tgt ccc aac tcc ttg att aaa gag ctc cat cac ttc agg     932
Val Ala Gly Cys Pro Asn Ser Leu Ile Lys Glu Leu His His Phe Arg
            265                 270                 275 att ctg gga gaa gag cag tac aac cgg tac cag cag tat ggt gca gag     980
Ile Leu Gly Glu Glu Gln Tyr Asn Arg Tyr Gln Gln Tyr Gly Ala Glu
        280                 285                 290 gag tgt gtc ctg cag atg ggg ggc gtg tta tgc ccc gcc cct ggc tgt    1028
Glu Cys Val Leu Gln Met Gly Gly Val Leu Cys Pro Arg Pro Gly Cys
        295                 300                 305 gga gcg ggg ctg ctg ccg gag cct gac cag agg aaa gtc acc tgc gaa    1076
Gly Ala Gly Leu Leu Pro Glu Pro Asp Gln Arg Lys Val Thr Cys Glu
```

```
                    310                 315                 320                 325
ggg ggc aat ggc ctg ggc tgt ggg ttt gcc ttc tgc cgg gaa tgt aaa        1124
Gly Gly Asn Gly Leu Gly Cys Gly Phe Ala Phe Cys Arg Glu Cys Lys
                330                 335                 340 gaa gcg tac cat gaa ggg gag tgc agt gcc gta ttt gaa gcc tca gga        1172
Glu Ala Tyr His Glu Gly Glu Cys Ser Ala Val Phe Glu Ala Ser Gly
            345                 350                 355 aca act act cag gcc tac aga gtc gat gaa aga gcc gcc gag cag gct        1220
Thr Thr Thr Gln Ala Tyr Arg Val Asp Glu Arg Ala Ala Glu Gln Ala
        360                 365                 370 cgt tgg gaa gca gcc tcc aaa gaa acc atc aag aaa acc acc aag ccc        1268
Arg Trp Glu Ala Ala Ser Lys Glu Thr Ile Lys Lys Thr Thr Lys Pro
    375                 380                 385 tgt ccc cgc tgc cat gta cca gtg gaa aaa aat gga ggc tgc atg cac        1316
Cys Pro Arg Cys His Val Pro Val Glu Lys Asn Gly Gly Cys Met His
390                 395                 400                 405 atg aag tgt ccg cag ccc cag tgc agg ctc gag tgg tgc tgg aac tgt        1364
Met Lys Cys Pro Gln Pro Gln Cys Arg Leu Glu Trp Cys Trp Asn Cys
                410                 415                 420 ggc tgc gag tgg aac cgc gtc tgc atg ggg gac cac tgg ttc gac gtg        1412
Gly Cys Glu Trp Asn Arg Val Cys Met Gly Asp His Trp Phe Asp Val
            425                 430                 435 tagccagggc ggccgggcgc ccatcgcca catcctgggg gagcataccc agtgtctacc       1472
ttcattttct aattctcttt tcaaacacac acacacacgc gcgcgcgcgc acacacactc      1532
ttcaagtttt tttcaaagtc caactacagc caaattgcag aagaaactcc tggatcccTT      1592
tcactatgtc catgaaaaac agcagagtaa aattacagaa gaagctcctg aatcccttTC      1652
agtttgtcca cacaagacag cagagccatc tgcgacacca ccaacaggcg ttctcagcct     1712
ccggatgaca caaataccag agcacagatt caagtgcaat ccatgtatct gtatgggtca     1772
ttctcacctg aattcgagac aggcagaatc agtagctgga gagagagttc tcacatttaa     1832
tatcctgcct tttaccttca gtaaacacca tgaagatgcc attgacaagg tgtttctctg     1892
taaaatgaac tgcagtgggt tctccaaact agattcatgg ctttaacagt aatgttctta     1952
tttaaatttt cagaaagcat ctattcccaa agaaccccag gcaatagtca aaacatttg     2012 tttatcctta agaattccat ctatataaat cgcattaatc gaaataccaa ctatgtgtaa     2072
atcaacttgt cacaaagtga gaaattatga agttaatttt gaatgttgaa tgtttgaatt     2132
acagggaaga aatcaagtta atgtactttc attccctttc atgatttgca actttagaaa     2192
gaaattgttt ttctgaaagt atcaccaaaa aatctatagt ttgattctga gtattcattt     2252
tgcaacttgg agattttgct aatacatttg gctccactgt aaatttaata gataaagtgc     2312
ctataaagga aacacgttta gaaatgattt caaaatgata ttcaatctta acaaaagtga     2372
acattattaa atcagaatct ttaaagagga gcctttccag aactaccaaa atgaagacac     2432
gcccgactct ctccatcaga agggtttata cccctttggc acaccctctc tgtccaatct     2492
gcaagtccca gggagctctg cataccaggg gttccccagg agagaccttc tcttaggaca     2552
gtaaactcac tagaatattc cttatgttga catggattgg atttcagttc aatcaaactt     2612 tcagctttttt ttcagccat tcacaacaca atcaaaagat taacaacact gcatgcggca     2672
aaccgcatgc tcttacccac actacgcaga agagaaagta caaccactat cttttgttct     2732
acctgtattg tctgacttct caggaagatc gtgaacataa ctgagggcat gagtctcact     2792
agcacatgga ggccctttg gatttagaga ctgtaaatta ttaaatcggc aacagggctt      2852 ctcttttttag atgtagcact gaaa                                            2876
```

<210> SEQ ID NO 4
<211> LENGTH: 437
<212> TYPE: PRT
<213> ORGANISM: Homo sapiens

<400> SEQUENCE: 4

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Glu Phe Phe Lys Cys Gly Ala His Pro Thr Ser Asp Lys
            180                 185                 190

Glu Thr Pro Val Ala Leu His Leu Ile Ala Thr Asn Ser Arg Asn Ile
        195                 200                 205

Thr Cys Ile Thr Cys Thr Asp Val Arg Ser Pro Val Leu Val Phe Gln
210                 215                 220

Cys Asn Ser Arg His Val Ile Cys Leu Asp Cys Phe His Leu Tyr Cys
225                 230                 235                 240

Val Thr Arg Leu Asn Asp Arg Gln Phe Val His Asp Pro Gln Leu Gly
                245                 250                 255

Tyr Ser Leu Pro Cys Val Ala Gly Cys Pro Asn Ser Leu Ile Lys Glu
            260                 265                 270

Leu His His Phe Arg Ile Leu Gly Glu Glu Gln Tyr Asn Arg Tyr Gln
        275                 280                 285

Gln Tyr Gly Ala Glu Glu Cys Val Leu Gln Met Gly Gly Val Leu Cys
290                 295                 300

Pro Arg Pro Gly Cys Gly Ala Gly Leu Leu Pro Glu Pro Asp Gln Arg
305                 310                 315                 320

Lys Val Thr Cys Glu Gly Gly Asn Gly Leu Gly Cys Gly Phe Ala Phe
                325                 330                 335

Cys Arg Glu Cys Lys Glu Ala Tyr His Glu Gly Glu Cys Ser Ala Val
            340                 345                 350

Phe Glu Ala Ser Gly Thr Thr Thr Gln Ala Tyr Arg Val Asp Glu Arg
        355                 360                 365

Ala Ala Glu Gln Ala Arg Trp Glu Ala Ala Ser Lys Glu Thr Ile Lys

```
                    370                 375                 380
Lys Thr Thr Lys Pro Cys Pro Arg Cys His Val Pro Val Glu Lys Asn
385                 390                 395                 400

Gly Gly Cys Met His Met Lys Cys Pro Gln Pro Gln Cys Arg Leu Glu
                    405                 410                 415

Trp Cys Trp Asn Cys Gly Cys Glu Trp Asn Arg Val Cys Met Gly Asp
                    420                 425                 430

His Trp Phe Asp Val
        435

<210> SEQ ID NO 5
<211> LENGTH: 21
<212> TYPE: DNA
<213> ORGANISM: Artificial sequence
<220> FEATURE:
<223> OTHER INFORMATION: oligonucleotide primer

<400> SEQUENCE: 5
agcctggtta agtccaagct g                                                21

<210> SEQ ID NO 6
<211> LENGTH: 22
<212> TYPE: DNA
<213> ORGANISM: Artificial sequence
<220> FEATURE:
<223> OTHER INFORMATION: oligonucleotide primer

<400> SEQUENCE: 6
gaaggtccca tttttcgttt tc                                               22

<210> SEQ ID NO 7
<211> LENGTH: 15
<212> TYPE: PRT
<213> ORGANISM: Artificial sequence
<220> FEATURE:
<223> OTHER INFORMATION: amino acid residue
<220> FEATURE:
<221> NAME/KEY: MISC_FEATURE
<222> LOCATION: (2)..(2)
<223> OTHER INFORMATION: Xaa may be a combination of any 2 amino acids
<220> FEATURE:
<221> NAME/KEY: MISC_FEATURE
<222> LOCATION: (4)..(4)
<223> OTHER INFORMATION: Xaa may be a combination of any 9 amino acids
<220> FEATURE:
<221> NAME/KEY: MISC_FEATURE
<222> LOCATION: (6)..(6)
<223> OTHER INFORMATION: Xaa may be any amino acid
<220> FEATURE:
<221> NAME/KEY: MISC_FEATURE
<222> LOCATION: (8)..(8)
<223> OTHER INFORMATION: Xaa may be any combination of 2 amino acids
<220> FEATURE:
<221> NAME/KEY: MISC_FEATURE
<222> LOCATION: (10)..(10)
<223> OTHER INFORMATION: Xaa may be any combination of 4 amino acids
<220> FEATURE:
<221> NAME/KEY: MISC_FEATURE
<222> LOCATION: (12)..(12)
<223> OTHER INFORMATION: Xaa may be any combination of 4 amino acids
<220> FEATURE:
<221> NAME/KEY: MISC_FEATURE
<222> LOCATION: (14)..(14)
<223> OTHER INFORMATION: Xaa may be any combination of 2 amino acids

<400> SEQUENCE: 7

Cys Xaa Cys Xaa Cys Xaa His Xaa Cys Xaa Cys Xaa Cys Xaa Cys
1               5                   10                  15
```

```
<210> SEQ ID NO 8
<211> LENGTH: 15
<212> TYPE: PRT
<213> ORGANISM: Artificial sequence
<220> FEATURE:
<223> OTHER INFORMATION: amino acid residue
<220> FEATURE:
<221> NAME/KEY: MISC_FEATURE
<222> LOCATION: (2)..(2)
<223> OTHER INFORMATION: Xaa may be any combination of 2 amino acids
<220> FEATURE:
<221> NAME/KEY: MISC_FEATURE
<222> LOCATION: (4)..(4)
<223> OTHER INFORMATION: Xaa may be any amino acid
<220> FEATURE:
<221> NAME/KEY: REPEAT
<222> LOCATION: (4)..(4)
<223> OTHER INFORMATION: Xaa may be repeated 9 to 399 times
<220> FEATURE:
<221> NAME/KEY: MISC_FEATURE
<222> LOCATION: (6)..(6)
<223> OTHER INFORMATION: Xaa may be any amino acid
<220> FEATURE:
<221> NAME/KEY: REPEAT
<222> LOCATION: (6)..(6)
<223> OTHER INFORMATION: Xaa may be repeated from 1 to 3 times
<220> FEATURE:
<221> NAME/KEY: MISC_FEATURE
<222> LOCATION: (8)..(8)
<223> OTHER INFORMATION: Xaa may be any amino acid
<220> FEATURE:
<221> NAME/KEY: REPEAT
<222> LOCATION: (8)..(8)
<223> OTHER INFORMATION: Xaa may be repeated from 2 to 3 times
<220> FEATURE:
<221> NAME/KEY: MISC_FEATURE
<222> LOCATION: (10)..(10)
<223> OTHER INFORMATION: Xaa may be any combination of 2 amino acids
<220> FEATURE:
<221> NAME/KEY: MISC_FEATURE
<222> LOCATION: (12)..(12)
<223> OTHER INFORMATION: Xaa may be any amino acid
<220> FEATURE:
<221> NAME/KEY: REPEAT
<222> LOCATION: (12)..(12)
<223> OTHER INFORMATION: Xaa may be repeated from 4 to 48 times
<220> FEATURE:
<221> NAME/KEY: MISC_FEATURE
<222> LOCATION: (14)..(14)
<223> OTHER INFORMATION: Xaa may be any combination of 2 amino acids

<400> SEQUENCE: 8

Cys Xaa Cys Xaa Cys Xaa His Xaa Cys Xaa Cys Xaa Cys Xaa Cys
1               5                   10                  15

<210> SEQ ID NO 9
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 1
<220> FEATURE:
<221> NAME/KEY: Intron
<222> LOCATION: (11)..(20)
<223> OTHER INFORMATION: Intron

<400> SEQUENCE: 9
accatgatag gtacgtgggt                                              20

<210> SEQ ID NO 10
<211> LENGTH: 20
<212> TYPE: DNA
```

```
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 2

<400> SEQUENCE: 10
ccttggtcag tgtttgtcag                                          20

<210> SEQ ID NO 11
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 2
<220> FEATURE:
<221> NAME/KEY: Intron
<222> LOCATION: (11)..(20)
<223> OTHER INFORMATION: Intron

<400> SEQUENCE: 11
gactgtgcag gtgagtctcc                                          20

<210> SEQ ID NO 12
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 3

<400> SEQUENCE: 12
tcccaaacag aattgtgacc                                          20

<210> SEQ ID NO 13
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 3
<220> FEATURE:
<221> NAME/KEY: Intron
<222> LOCATION: (11)..(20)
<223> OTHER INFORMATION: Intron

<400> SEQUENCE: 13
ggaagtccag gtaattggaa                                          20

<210> SEQ ID NO 14
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
```

```
<222> LOCATION: (11)..(20)
<223> OTHER INFORMATION: Exon 4

<400> SEQUENCE: 14
tcttctccag caggtagatc                                                 20

<210> SEQ ID NO 15
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 4
<220> FEATURE:
<221> NAME/KEY: Intron
<222> LOCATION: (11)..(20)
<223> OTHER INFORMATION: Intron

<400> SEQUENCE: 15
cttgacccag gtaaggaaat                                                 20

<210> SEQ ID NO 16
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 5

<400> SEQUENCE: 16
tttcccaaag ggtccatctt                                                 20

<210> SEQ ID NO 17
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 5
<220> FEATURE:
<221> NAME/KEY: Intron
<222> LOCATION: (11)..(20)
<223> OTHER INFORMATION: Intron

<400> SEQUENCE: 17
gactagtgca gtaagtacct                                                 20

<210> SEQ ID NO 18
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 6

<400> SEQUENCE: 18
tttctttcag gaattttct                                                  20
```

```
<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 6
<220> FEATURE:
<221> NAME/KEY: Intron
<222> LOCATION: (11)..(20)
<223> OTHER INFORMATION: Intron

<400> SEQUENCE: 19
cagacgtcag gtaaggatct                                               20

<210> SEQ ID NO 20
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 7

<400> SEQUENCE: 20
ctctctgcag gagccccgtc                                               20

<210> SEQ ID NO 21
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 7
<220> FEATURE:
<221> NAME/KEY: Intron
<222> LOCATION: (11)..(20)
<223> OTHER INFORMATION: Intron

<400> SEQUENCE: 21
ccttgtgtgg gtaagtctag                                               20

<210> SEQ ID NO 22
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 8

<400> SEQUENCE: 22
tttccaacag ctggctgtcc                                               20

<210> SEQ ID NO 23
<211> LENGTH: 20
<212> TYPE: DNA
<213> ORGANISM: Homo sapiens
<220> FEATURE:
<221> NAME/KEY: misc_feature
```

```
<222> LOCATION: (1)..(10)
<223> OTHER INFORMATION: Exon 8
<220> FEATURE:
<221> NAME/KEY: Intron
<222> LOCATION: (11)..(20)
<223> OTHER INFORMATION: Intron

<400> SEQUENCE: 23
agaagagcag gtgagtgagc                                                    20

<210> SEQ ID NO 24
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 9

<400> SEQUENCE: 24
ggttttgcag tacaaccggt                                                    20

<210> SEQ ID NO 25
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 9
<220> FEATURE:
<221> NAME/KEY: Intron
<222> LOCATION: (11)..(20)
<223> OTHER INFORMATION: Intron

<400> SEQUENCE: 25
gggctgtggg gtgagtactg                                                    20

<210> SEQ ID NO 26
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 10

<400> SEQUENCE: 26
tcttttgcag tttgccttct                                                    20

<210> SEQ ID NO 27
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 10
<220> FEATURE:
<221> NAME/KEY: Intron
<222> LOCATION: (11)..(20)
<223> OTHER INFORMATION: Intron
```

```
<400> SEQUENCE: 27
aactactcag gtacagaatg                                               20

<210> SEQ ID NO 28
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 11

<400> SEQUENCE: 28
gtttccccag gcctacagag                                               20

<210> SEQ ID NO 29
<211> LENGTH: 20
<212> TYPE: DNA
<213> ORGANISM: Homo sapiens
<220> FEATURE:
<221> NAME/KEY: misc_feature
<222> LOCATION: (1)..(10)
<223> OTHER INFORMATION: Exon 11
<220> FEATURE:
<221> NAME/KEY: Intron
<222> LOCATION: (11)..(20)
<223> OTHER INFORMATION: Intron

<400> SEQUENCE: 29
gaaaaaaatg gtgagtctgt                                               20

<210> SEQ ID NO 30
<211> LENGTH: 20
<212> TYPE: DNA
<213> ORGANISM: Homo sapiens
<220> FEATURE:
<221> NAME/KEY: Intron
<222> LOCATION: (1)..(10)
<223> OTHER INFORMATION: Intron
<220> FEATURE:
<221> NAME/KEY: misc_feature
<222> LOCATION: (11)..(20)
<223> OTHER INFORMATION: Exon 12

<400> SEQUENCE: 30
cccccaacag gaggctgcat                                               20

<210> SEQ ID NO 31
<211> LENGTH: 23
<212> TYPE: DNA
<213> ORGANISM: Artificial sequence
<220> FEATURE:
<223> OTHER INFORMATION: oligonucleotide primer

<400> SEQUENCE: 31
tgatagtcat aactgtgtgt aag                                           23

<210> SEQ ID NO 32
<211> LENGTH: 23
<212> TYPE: DNA
<213> ORGANISM: Artificial sequence
<220> FEATURE:
<223> OTHER INFORMATION: oligonucleotide primer

<400> SEQUENCE: 32
```

```
acagggaaca taaactctga tcc                                    23

<210> SEQ ID NO 33
<211> LENGTH: 22
<212> TYPE: DNA
<213> ORGANISM: Artificial sequence
<220> FEATURE:
<223> OTHER INFORMATION: oligonucleotide primer

<400> SEQUENCE: 33
caacacacca ggcaccttca ga                                     22

<210> SEQ ID NO 34
<211> LENGTH: 19
<212> TYPE: DNA
<213> ORGANISM: Artificial sequence
<220> FEATURE:
<223> OTHER INFORMATION: oligonucleotide primer

<400> SEQUENCE: 34
gtttgggaat gcgtgtttt                                         19

<210> SEQ ID NO 35
<211> LENGTH: 24
<212> TYPE: DNA
<213> ORGANISM: Artificial sequence
<220> FEATURE:
<223> OTHER INFORMATION: oligonucleotide primer

<400> SEQUENCE: 35
agaattagaa aatgaaggta gaca                                   24

<210> SEQ ID NO 36
<211> LENGTH: 24
<212> TYPE: DNA
<213> ORGANISM: Artificial sequence
<220> FEATURE:
<223> OTHER INFORMATION: oligonucleotide primer

<400> SEQUENCE: 36
gcgcggctgg cgccgctgcg cgca                                   24

<210> SEQ ID NO 37
<211> LENGTH: 20
<212> TYPE: DNA
<213> ORGANISM: Artificial sequence
<220> FEATURE:
<223> OTHER INFORMATION: oligonucleotide primer

<400> SEQUENCE: 37
gcggcgcaga gaggctgtac                                        20

<210> SEQ ID NO 38
<211> LENGTH: 23
<212> TYPE: DNA
<213> ORGANISM: Artificial sequence
<220> FEATURE:
<223> OTHER INFORMATION: oligonucleotide primer

<400> SEQUENCE: 38
atgttgctat caccatttaa ggg                                    23

<210> SEQ ID NO 39
<211> LENGTH: 23
<212> TYPE: DNA
```

<213> ORGANISM: Artificial sequence
<220> FEATURE:
<223> OTHER INFORMATION: oligonucleotide primer

<400> SEQUENCE: 39
agattggcag cgcaggcggc atg                                        23

<210> SEQ ID NO 40
<211> LENGTH: 21
<212> TYPE: DNA
<213> ORGANISM: Artificial sequence
<220> FEATURE:
<223> OTHER INFORMATION: oligonucleotide primer

<400> SEQUENCE: 40
acatgtcact tttgcttccc t                                          21

<210> SEQ ID NO 41
<211> LENGTH: 23
<212> TYPE: DNA
<213> ORGANISM: Artificial sequence
<220> FEATURE:
<223> OTHER INFORMATION: oligonucleotide primer

<400> SEQUENCE: 41
aggccatgct ccatgcagac tgc                                        23

<210> SEQ ID NO 42
<211> LENGTH: 24
<212> TYPE: DNA
<213> ORGANISM: Artificial sequence
<220> FEATURE:
<223> OTHER INFORMATION: oligonucleotide primer

<400> SEQUENCE: 42
acaagctttt aaagagtttc ttgt                                       24

<210> SEQ ID NO 43
<211> LENGTH: 20
<212> TYPE: DNA
<213> ORGANISM: Artificial sequence
<220> FEATURE:
<223> OTHER INFORMATION: oligonucleotide primer

<400> SEQUENCE: 43
aggcaatgtg ttagtacaca                                            20

<210> SEQ ID NO 44
<211> LENGTH: 22
<212> TYPE: DNA
<213> ORGANISM: Artificial sequence
<220> FEATURE:
<223> OTHER INFORMATION: oligonucleotide primer

<400> SEQUENCE: 44
acatgtctta aggagtacat tt                                         22

<210> SEQ ID NO 45
<211> LENGTH: 24
<212> TYPE: DNA
<213> ORGANISM: Artificial sequence
<220> FEATURE:
<223> OTHER INFORMATION: oligonucleotide primer

<400> SEQUENCE: 45
tctctaattt cctggcaaac agtg                                       24

<210> SEQ ID NO 46
<211> LENGTH: 23
<212> TYPE: DNA
<213> ORGANISM: Artificial sequence
<220> FEATURE:
<223> OTHER INFORMATION: oligonucleotide primer

<400> SEQUENCE: 46
agagattgtt tactgtggaa aca                                          23

<210> SEQ ID NO 47
<211> LENGTH: 23
<212> TYPE: DNA
<213> ORGANISM: Artificial sequence
<220> FEATURE:
<223> OTHER INFORMATION: oligonucleotide primer

<400> SEQUENCE: 47
gagtgatgct atttttagat cct                                          23

<210> SEQ ID NO 48
<211> LENGTH: 24
<212> TYPE: DNA
<213> ORGANISM: Artificial sequence
<220> FEATURE:
<223> OTHER INFORMATION: oligonucleotide primer

<400> SEQUENCE: 48
tgcctttcca cactgacagg tact                                         24

<210> SEQ ID NO 49
<211> LENGTH: 24
<212> TYPE: DNA
<213> ORGANISM: Artificial sequence
<220> FEATURE:
<223> OTHER INFORMATION: oligonucleotide primer

<400> SEQUENCE: 49
tctgttcttc attagcatta gaga                                         24

<210> SEQ ID NO 50
<211> LENGTH: 23
<212> TYPE: DNA
<213> ORGANISM: Artificial sequence
<220> FEATURE:
<223> OTHER INFORMATION: oligonucleotide primer

<400> SEQUENCE: 50
tgatagtcat aactgtgtgt aag                                          23

<210> SEQ ID NO 51
<211> LENGTH: 23
<212> TYPE: DNA
<213> ORGANISM: Artificial sequence
<220> FEATURE:
<223> OTHER INFORMATION: oligonucleotide primer

<400> SEQUENCE: 51
actgtctcat tagcgtctat ctt                                          23

<210> SEQ ID NO 52
<211> LENGTH: 20
<212> TYPE: DNA
<213> ORGANISM: Artificial sequence
<220> FEATURE:

<223> OTHER INFORMATION: oligonucleotide primer

<400> SEQUENCE: 52
gggtgaaatt tgcagtcagt                  20

<210> SEQ ID NO 53
<211> LENGTH: 23
<212> TYPE: DNA
<213> ORGANISM: Artificial sequence
<220> FEATURE:
<223> OTHER INFORMATION: oligonucleotide primer

<400> SEQUENCE: 53
aatataatcc cagcccatgt gca              23

<210> SEQ ID NO 54
<211> LENGTH: 22
<212> TYPE: DNA
<213> ORGANISM: Artificial sequence
<220> FEATURE:
<223> OTHER INFORMATION: oligonucleotide primer

<400> SEQUENCE: 54
attgccaaat gcaacctmtg tc               22

<210> SEQ ID NO 55
<211> LENGTH: 22
<212> TYPE: DNA
<213> ORGANISM: Artificial sequence
<220> FEATURE:
<223> OTHER INFORMATION: oligonucleotide primer

<400> SEQUENCE: 55
ttggaggaat gagtagggca tt               22

<210> SEQ ID NO 56
<211> LENGTH: 23
<212> TYPE: DNA
<213> ORGANISM: Artificial sequence
<220> FEATURE:
<223> OTHER INFORMATION: oligonucleotide primer

<400> SEQUENCE: 56
acagggaaca taaactctga tcc              23

<210> SEQ ID NO 57
<211> LENGTH: 22
<212> TYPE: DNA
<213> ORGANISM: Artificial sequence
<220> FEATURE:
<223> OTHER INFORMATION: oligonucleotide primer

<400> SEQUENCE: 57
caacacacca ggcaccttca ga               22

<210> SEQ ID NO 58
<211> LENGTH: 19
<212> TYPE: DNA
<213> ORGANISM: Artificial sequence
<220> FEATURE:
<223> OTHER INFORMATION: oligonucleotide primer

<400> SEQUENCE: 58
gtttgggaat gcgtgtttt                   19

```
<210> SEQ ID NO 59
<211> LENGTH: 24
<212> TYPE: DNA
<213> ORGANISM: Artificial sequence
<220> FEATURE:
<223> OTHER INFORMATION: oligonucleotide primer

<400> SEQUENCE: 59
agaattagaa aatgaaggta gaca                                              24

<210> SEQ ID NO 60
<211> LENGTH: 76
<212> TYPE: PRT
<213> ORGANISM: Homo sapiens

<400> SEQUENCE: 60
```

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

```
<210> SEQ ID NO 61
<211> LENGTH: 76
<212> TYPE: PRT
<213> ORGANISM: Saccharomyces sp.

<400> SEQUENCE: 61
```

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

```
<210> SEQ ID NO 62
<211> LENGTH: 76
<212> TYPE: PRT
<213> ORGANISM: Glycine sp.

<400> SEQUENCE: 62
```

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly
65                  70                  75

<210> SEQ ID NO 63
<211> LENGTH: 33
<212> TYPE: DNA
<213> ORGANISM: Homo sapiens

<400> SEQUENCE: 63
caccagctgg aagtccaggg tccatcttgc tgg                          33

<210> SEQ ID NO 64
<211> LENGTH: 40
<212> TYPE: DNA
<213> ORGANISM: Homo sapiens

<400> SEQUENCE: 64
tcccaaaggg tccatcttgc tgggatgatg ttttaattcc                   40

<210> SEQ ID NO 65
<211> LENGTH: 40
<212> TYPE: DNA
<213> ORGANISM: Homo sapiens

<400> SEQUENCE: 65
tcccaaaggt ccatcttgct gggatgatgt tttaattcca                   40

<210> SEQ ID NO 66
<211> LENGTH: 38
<212> TYPE: DNA
<213> ORGANISM: Homo sapiens
<220> FEATURE:
<221> NAME/KEY: Intron
<222> LOCATION: (1)..(8)
<223> OTHER INFORMATION: Intron
<220> FEATURE:
<221> NAME/KEY: exon
<222> LOCATION: (9)..(38)
<223> OTHER INFORMATION: Exon 5

<400> SEQUENCE: 66 tcccaaag ggt cca tct tgc tgg gat gat gtt tta att              38
         Gly Pro Ser Cys Trp Asp Asp Val Leu Ile
         1               5                   10

<210> SEQ ID NO 67
<211> LENGTH: 10
<212> TYPE: PRT
<213> ORGANISM: Homo sapiens

<400> SEQUENCE: 67

Gly Pro Ser Cys Trp Asp Asp Val Leu Ile
1               5                   10

<210> SEQ ID NO 68
<211> LENGTH: 37
<212> TYPE: DNA
<213> ORGANISM: Homo sapiens
<220> FEATURE:
<221> NAME/KEY: Intron
<222> LOCATION: (1)..(8)
<223> OTHER INFORMATION: Intron
<220> FEATURE:
<221> NAME/KEY: exon
<222> LOCATION: (9)..(24)
<223> OTHER INFORMATION: Exon 5

<400> SEQUENCE: 68 tcccaaag gtc cat ctt gct ggg atg atg ttt taatt                37

```
           Val His Leu Ala Gly Met Met Phe
             1               5
```

<210> SEQ ID NO 69
<211> LENGTH: 8
<212> TYPE: PRT
<213> ORGANISM: Homo sapiens

<400> SEQUENCE: 69

```
Val His Leu Ala Gly Met Met Phe
  1               5
```

<210> SEQ ID NO 70
<211> LENGTH: 21
<212> TYPE: DNA
<213> ORGANISM: Homo sapiens

<400> SEQUENCE: 70
gggacagcca gccacacaag g                                        21